US010023916B2

(12) United States Patent
Frendewey et al.

(10) Patent No.: US 10,023,916 B2
(45) Date of Patent: Jul. 17, 2018

(54) MARKERS OF TUMOR CELL RESPONSE TO ANTI-CANCER THERAPY

(71) Applicant: Regeneron Pharmaceuticals, Inc., Tarrytown, NY (US)

(72) Inventors: David Frendewey, New York, NY (US); Gavin Thurston, Briarcliff Manor, NY (US); George D. Yancopoulos, Yorktown Heights, NY (US); Matthew Koss, Mount Kisco, NY (US); Gustavo Droguett, New City, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 286 days.

(21) Appl. No.: 14/253,592

(22) Filed: Apr. 15, 2014

(65) Prior Publication Data
US 2014/0308370 A1    Oct. 16, 2014

Related U.S. Application Data

(60) Provisional application No. 61/812,033, filed on Apr. 15, 2013.

(51) Int. Cl.
*C12Q 1/68* (2018.01)
*C12P 19/34* (2006.01)
*A61K 38/00* (2006.01)
*G01N 33/566* (2006.01)
*C12Q 1/6886* (2018.01)

(52) U.S. Cl.
CPC ..... *C12Q 1/6886* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2007/0134670 A1* | 6/2007 | Kasper | C12Q 1/6886 435/6.14 |
| 2010/0004253 A1* | 1/2010 | Aziz | C12Q 1/485 514/252.1 |
| 2012/0231970 A1 | 9/2012 | Nakagama et al. | |
| 2012/0264131 A1 | 10/2012 | Goel et al. | |

FOREIGN PATENT DOCUMENTS

| WO | WO 2006009805 A2 | 1/2006 |
| WO | WO 2007/035709 A2 | 3/2007 |
| WO | WO 2008008430 A2 | 1/2008 |
| WO | WO 2008/143795 A1 | 11/2008 |
| WO | WO 2009108860 A2 | 9/2009 |
| WO | WO 2009147525 A1 | 12/2009 |
| WO | WO 2010068473 A1 | 6/2010 |
| WO | WO 2011156777 A1 | 12/2011 |
| WO | WO 2012/170711 A1 | 12/2012 |
| WO | WO 2012174293 A2 | 12/2012 |
| WO | WO 2014/078850 * | 5/2014 |
| WO | WO 2014172376 A2 | 10/2014 |

OTHER PUBLICATIONS

Daimandis (Mol Cancer Res 8(9) Sep. 2010 pp. OF1-OF13).*
Tentler (Nature Reviews Clinical Oncology vol. 9 Jun. 2012 pp. 33-349).*
Bogner (Biochemical and Biophysical Research Communications 386 (2009) pp. 305-310).*
Ghorai (Frontiers in Genetics Apr. 2014 vol. 5 article 100).*
Pompili (Journal of Experimental and Clinical Cancer Research (2016) 35:189).*
Wang (PloS ONE Jul. 2012 7(7);e41561).*
Aushev, V., et al., "Comparisons of microRNA Patterns in Plasma before and after Tumor Removal Reveal New Biomarkers of Lung Squamous Cell Carcinoma," *PLOS ONE*, 2013, vol. 8 (10), pp. 1-10.
Bhatt, A., et al., "Cancer biomarkers—Current perspectives," *Indian J Med Res*, 2010, vol. 132, pp. 129-149.
Cabral, R., et al., "Circulating DNA as a Biomarker for Early Detection of Cancer: A Brief Update with an Emphasis on Lung Cancer," *The Open Lung Cancer Journal*, 2010, vol. 3, pp. 38-44.
Duttagupta, R., et al., "Impact of Cellular miRNAs on Circulating miRNA Biomarker Signatures," *PLOS ONE*, 2011, vol. 6(6), pp. 1-14.
Gormally, E., et al., "Circulating free DNA in plasma or serum as biomarker of carcinogenesis: Practical aspects and biological significance," *Mutat Res.*, 2007, vol. 635(2-3), pp. 105-117.
Holleman, A., et al., "The expression of 70 apoptosis genes in relation to lineage, genetic subtype, cellular drug resistance, and outcome in childhood acute lymphoblastic leukemia," *Blood*, 2006, vol. 107(2), pp. 769-776.
Mo, M., et al., "Cell-free Circulating MiRNA Biomarkers in Cancer," *Journal of Cancer*, 2012, vol. 3, pp. 432-448.
Moldovan, L., et al., "Analyzing the Circulating MicroRNAs in Exosomes/Extracellular Vesicles from Serum or Plasma by qRT-PCR," *Methods Mol Biol.*, 2013, vol. 1024, pp. 129-145.
Moyano, J., et al., "αB-crystallin is a novel oncoprotein that predicts poor clinical outcome in breast cancer," *J. Clin. Invest.*, 2006, vol. 116(1), pp. 261-270.
Osman, I., et al., "Serum levels of shed HER2/NEU protein in men with prostate cancer correlate with disease progression," *J. Urol.*, 2005, vol. 174, pp. 2174-2177, abstract only.

(Continued)

Primary Examiner — Stephen T Kapushoc
(74) Attorney, Agent, or Firm — Yongjin Choi; Alston & Bird LLP

(57) ABSTRACT

Compositions and methods for determining circulating biomolecules before, during, and/or after treatment of a patient with an anti-cancer or anti-tumor drug (or putative drug) are described. Methods of treatments based on the compositions and methods described herein are also provided. Noninvasive methods and kits are provided for assessing the efficacy of an anti-cancer therapy for killing or damaging cancer cells. Embodiments are used to determine the cancer-killing efficacy of an anti-cancer drug in a patient, to optimize the selection of an anti-cancer drug for treatment of a patient, to adjust the dosage of an anti-cancer drug for treatment of a particular cancer in a patient and for identifying useful anti-cancer therapeutics for any one particular type of cancer.

3 Claims, 8 Drawing Sheets

(56) References Cited

OTHER PUBLICATIONS

Pavlou, M., et al., "The cancer cell secretome: A good source for discovering biomarkers?," *Journal of Proteomics*, 2010, vol. 73, pp. 1896-1906.
Sapre, N., et al., "Circulating MicroRNAs as Biomarkers of Prostate Cancer: The State of Play," *Prostate Cancer*, 2013, vol. 2013, pp. 1-10.
Schwarzenbach, H., et al., "Cell-free nucleic acids as biomarkers in cancer patients," *Nature Reviews Cancer*, 2011, vol. 6, pp. 426-437.
Whitfield, M., et al., "Common markers of proliferation," *Nature Reviews/Cancer*, 2006, vol. 6, pp. 99-106.
Xue, H., et al., "The cancer secretome: a reservoir of biomarkers," *Journal of Translational Medicine*, 2008, vol. 6(52), pp. 1-12.
PCT/US2014/034217 International Search Report dated Nov. 13, 2014.
PCT/US2014/034217 Written Opinion of the International Searching Authority dated Nov. 13, 2014.
EP Supplemental Partial European Search Report for application EP14784689 dated Oct. 12, 2016.
PCT/US2014/034217 International Preliminary Report on Patentability dated Oct. 20, 2015.
EP Supplementary European Search Report for application EP14784689 dated Jan. 26, 2017.
Wei, et al., "Reduction of Plasma MicroRNA-21 is Associated with Chemotherapeutic Response in Patients with Non-small Cell Lung Cancer," *Chinese Journal of Cancer Research*, 2011, 23(2):123-128.
Komatsu, et al., "Circulating microRNAs in plasma of patients with oesophageal squamous cell carcinoma," *British Journal of Cancer*, 2011, 105(1):104-111.
Wei, et al., "Identification of plasma microRNA-21 as a biomarker for early detection and chemosensitivity of non-small cell lung cancer," 2011, *Chin J Cancer*, 30(6):407-414.
Hummel, et al., "MicroRNAs: predictors and modifiers of chemo- and radiotherapy in different tumor types," *European Journal of Cancer*, 46(2):298-311, (2010).
Boren, et al., "MicroRNAs and their target messenger RNAs associated with ovarian cancer response to chemotherapy," *Gynecologic Oncology*, 113(2):249-255, (2009).
Ponomareva, et al., "Molecular-genetic markers in the diagnosis of lung cancer" *Molecular Biology*, 45(2):203-217, (2011).
Edwards, et al., "A systematic review of treatment guidelines for metastatic colorectal cancer," *Colorectal Disease*, 14, e31-e47, (2011).

\* cited by examiner

MARKERS OF TUMOR CELL RESPONSE TO ANTI-CANCER THERAPY

TECHNICAL FIELD

Methods provided herein are useful in the field of cancer and cancer therapeutics, and in particular, in determining efficacy of cancer therapeutics. Methods and compositions for measuring circulating biomolecules such as, e.g., nucleic acids and proteins, in conjunction with anti-cancer therapy.

BACKGROUND

The term cancer commonly refers to a broad group of diseases characterized by unregulated cell growth that forms malignant tumors. Cancer therapies generally kill cells, ideally primarily tumor cells but also normal cells. Current methods for determining the effectiveness of cancer therapy include invasive procedures such as biopsies, as well as imaging methods such as CT scan, magnetic resonance imaging (MRI) scan, and positron emissions tomography (PET) scan. However, to take advantage of such non-invasive methods, the tumors typically must reduce in size enough that the imaging procedures can detect a difference. To aid in determining whether a new anti-cancer drug or anti-tumor drug has efficacy in killing cancer or tumor cells, or whether an anti-cancer drug or anti-tumor drug has efficacy against a particular tumor or cancer, it would be very useful to have a method to determine non-invasively the amount of tumor or cancer cell killing in a patient relative to normal cell killing. Methods and compositions for non-invasive determination of circulating biomolecules following tumor or cancer cell killing by a therapeutic or putative therapeutic are also desirable.

MicroRNAs are small (approximately 22 nucleotide) single-stranded RNAs found predominantly in the cytoplasm of higher eukaryotes (plants and multi-cellular animals). Their primary function is to regulate gene expression by binding to specific target mRNAs, usually in the 3'-untranscribed region (3'-UTR), and inhibiting their translation while promoting their destruction. There are over 1,000 identified miRNAs in mouse and over 2,000 in humans. Most miRNAs are thought to have multiple mRNA targets that could number in the hundreds. Many mRNAs that are regulated by miRNAs have binding sites in their 3'-UTRs for multiple miRNAs. Some miRNAs are fairly ubiquitously expressed; others exhibit highly restricted tissue-specific expression.

Recent research has discovered that a subset of a few hundred miRNAs is present and readily detectable in the serum and plasma of mammals. The profile of the serum/plasma miRNAs is remarkably stable in normal healthy animals, but can vary in disease states or in response to drugs or chemically induced toxicities. The serum/plasma miRNA profile differs from that for the cellular component of the blood.

A growing literature is beginning to reveal many examples of serum/plasma miRNA profiles that provide biomarkers for diagnosis and prognosis in diseases such as liver fibrosis, myocardial malfunction, and various cancers. Serum/plasma miRNA profiling has also been shown to predict drug efficacy, toxicity, and specific organ and tissue damage.

SUMMARY

In various aspects, compositions and methods for determining circulating biomolecules before, during, and/or after treatment of a patient with an anti-cancer or anti-tumor drug (or putative drug) are described. Methods of treatments based on the compositions and methods described herein are also provided. Aspects and embodiments that are directed to anti-cancer therapy, whether expressly stated or not, are aspects and embodiments that may be directed to anti-tumor therapies as well. Similarly, aspects and embodiments that employ anti-cancer drugs may also be employed with anti-tumor drugs.

In various aspects, noninvasive methods and kits are provided for assessing the efficacy of an anti-cancer therapy for killing or damaging cancer cells. Embodiments are used to determine the cancer-killing efficacy of an anti-cancer drug in a patient, to optimize the selection of an anti-cancer drug for treatment of a patient, to adjust the dosage of an anti-cancer drug for treatment of a particular cancer in a patient and for identifying useful anti-cancer therapeutics for any one particular type of cancer.

Provided herein are noninvasive methods for determining cancer-killing efficacy in a patient treated with an anti-cancer therapy and in particular an anti-cancer drug. In some embodiments, the methods comprise measuring a blood level of an intracellular cancer cell-specific marker in the patient following administration of a putative anti-cancer drug. In some embodiments, the level of a tumor cell-specific marker can be measured before and after administration of an anti-cancer drug. Changes in the level of such a tumor cell-specific marker can be indicative of efficacy of the putative anti-cancer drug. An increase in the level of the intracellular cancer cell-specific marker in the blood of the patient compared to a control marker is indicative of efficacy of the putative anti-cancer drug. In other embodiments, a decrease in the level of the intracellular cancer cell-specific marker in a sample compared to a control marker is indicative of efficacy of the putative anti-cancer drug. In certain embodiments, changes in the level of a tumor cell-specific marker correlates with therapeutic efficacy of the anti-tumor drug.

The patient can be treated with the putative anti-cancer drug if the level of intracellular cancer cell-specific marker in the patient's circulation increases following administration of the putative anti-cancer drug in relation to the control marker. Alternatively, patients can be treated with the putative anti-cancer drug if the level of cancer cell-specific marker in a sample decreases following administration of the putative anti-cancer drug in relation to the control marker. In some embodiments, the anti-cancer drug is an anti-tumor drug conjugate of an antigen-binding protein and a drug, the cancer cell-specific marker is a tumor-specific marker, and the cancer is a solid tumor or a B-cell related cancer. In certain embodiments, the cancer cell-specific marker is a micro RNA (miRNA).

Also provided are noninvasive methods of selecting an effective anti-cancer drug for treatment of a patient in need thereof. In some embodiments, the methods comprise measuring a first level of a cancer cell-specific marker in a first sample from a cancer-bearing patient, administering a putative anti-cancer drug to the patient, and measuring a second level of the cancer cell-specific marker in a second sample from the patient. An increase in the second level indicates anti-cancer efficacy of the putative anti-cancer drug and the patient is treated with the putative anti-cancer drug, thereby selecting an effective anti-cancer drug for treatment of the patient. In some embodiments, the increase in the level of the cancer cell-specific marker in the blood of the patient is compared to a corresponding change in a control marker. Depending on the marker selected, a decrease in the second level can indicate efficacy of the putative anti-cancer drug such that patients are treated with the putative anti-cancer drug, thereby selecting an effective anti-cancer drug for treatment of the patient. In certain embodiments the marker measured to determine efficacy of the anti-cancer drug is a tumor-responsive biomarker. In some embodiments, the anti-cancer drug is an anti-tumor drug conjugate of an antigen-binding protein and a drug, the cancer cell-specific marker is a tumor-specific marker, and the cancer is a solid tumor or a B-cell related cancer. In one embodiment, a control marker is a marker from a non-cancer (or non-tumor) cell.

Further provided are noninvasive methods of adjusting a dosage of an anti-cancer drug for treatment of a cancer in a patient. In some embodiments, the methods comprise measuring a level of one or more cancer cell-specific markers in the circulation of a patient who has been administered an initial amount of the anti-cancer drug, and adjusting the dosage for subsequent administration of the anti-cancer drug to the patient based upon the level of the one or more cancer cell-specific markers in the circulation of the patient after administration of the initial amount of the anti-cancer drug. In some embodiments, the methods further comprise measuring at least one control marker in the circulation for normalization of the level of the one or more cancer cell-specific markers. In certain embodiments the marker measured to determine efficacy of the anti-cancer drug is a tumor-responsive biomarker. In some embodiments, the anti-cancer drug is an anti-tumor drug conjugate of an antigen-binding protein and a drug, the cancer cell-specific marker is a tumor-specific marker, and the cancer is a solid tumor or a B-cell related cancer.

For example, patients having a higher level of a tumor-responsive biomarker after the first administration of the anti-tumor drug could, on average, receive a greater second dose of the anti-tumor drug than patients having a lower level of the tumor-responsive biomarker after the first dose of the anti-tumor drug. Alternatively, depending on the individual marker, patients having a lower level of the tumor-responsive biomarker after the first administration of the anti-tumor drug could, on average, receive a greater second dose of the anti-tumor drug than patients having a higher level of the tumor-responsive biomarker after the first dose of the anti-tumor drug.

Still further provided are noninvasive methods for assessing a therapeutic efficacy of an anti-cancer drug in a patient. In some embodiments, the methods comprise (a) obtaining a first baseline sample from the patient's circulation, wherein the patient has cancer (or a tumor); (b) administering to the patient a dose of an anti-cancer drug, wherein at least one cancer cell-specific marker is sequestered within the cancer cell of the patient prior to administration of the anti-cancer drug but is released into the patient's circulation following administration of the anti-cancer drug; (c) obtaining a second sample from the patient's circulation; (d) measuring an amount of the at least one cancer cell-specific marker (i) in the first baseline sample and (ii) in the second sample, and (e) comparing the amount of the cancer cell-specific marker in the first baseline sample with the amount of the cancer cell-specific marker in the second sample. An increase in the amount of the at least one cancer cell-specific marker in the second sample relative to the amount of the at least one cancer cell-specific marker in the first baseline sample is indicative of increased cancer cell death in the patient. The patient can be treated with the anti-cancer drug that increases the at least one cancer cell-specific marker. Alternatively, depending on the individual marker, patients having a lower level of the biomarker after the first administration of the anti-tumor drug could, on average, receive a greater second dose of the anti-tumor drug than patients having a higher level of the biomarker after the first dose of the anti-tumor drug. In some embodiments, the anti-cancer drug is an anti-cancer drug conjugate of an antigen-binding protein and a drug, the cancer cell-specific marker is a tumor-specific marker, and the cancer is a solid tumor or a B-cell related cancer. Also provided herein are tumor-responsive biomarkers that can change in response to the tumor burden, but are not necessarily derived from the tumor.

It is also contemplated that embodiments herein can be used to identify anti-cancer drugs with high efficacy on particular types of cancer. In particular, a subject, typically a mouse or other rodent having a pre-determined form of cancer, is tested for a baseline level of one or more biomolecules associated with the pre-determined form of cancer, e.g., a CD20 marker for lymphoma. The proposed anti-cancer drug for the pre-determined form of cancer is administered to the subject and the level of the biomolecule determined. Increases or decreases of the biomolecule compared to control markers are used to identify anti-cancer drugs with greater potency for killing or damaging the pre-determined form of cancer in the subject. Alternatively, increases or decreases of the biomolecule before and after administration of the anti-cancer drug can be used to identify candidate anti-cancer drugs with greater potency for killing or damaging the pre-determined form of cancer cells in the subject. It is contemplated that a plurality of anti-cancer drugs can be tested using this method to identify and screen for anti-cancer drugs having enhanced efficacy for various forms of cancer. In addition, anti-cancer drugs having greater efficacy for one type of cancer over another type of cancer can also be identified, thereby maximizing cancer cell killing and damage, for any one anti-cancer drug.

In one aspect, a method for selecting an anti-cancer drug for treatment of a human tumor is provided, comprising introducing into a suitable host non-human animal (e.g., any rodent or mouse) a xenograft of the human tumor, administering a putative or candidate anti-cancer agent to the xenografted host non-human animal (e.g., a mouse), and determining the level of one or more intracellular tumor markers that have entered the mouse's circulation from a cell of the xenograft, wherein a putative anti-tumor agent that releases a predetermined level of one or more of the intracellular tumor cell markers from the cell of the xenograft is selected as a suitable therapeutic for treating the human tumor. In some embodiments, a tumor cell, a tumor tissue, or a tumor organ can be introduced onto any host animal, (e.g., any rodent) in order to determine the effectiveness of an anti-tumor drug by measuring the level of a tumor-cell specific marker before and after administration of the anti-tumor drug.

In another embodiment, a putative or candidate anti-cancer drug is selected based on the level of a cell-specific marker before and after administration of a drug to a host non-human animal (e.g., any rodent) xenografted with a tumor cell, a tumor tissue, or a tumor organ. For example, in some embodiments, an anti-cancer drug is selected wherein the level of a tumor cell-specific marker is decreased following administration of the putative anti-tumor agent to a xenografted host non-human animal (e.g., any rodent) compared to the level of tumor cell-specific marker prior to administration of the candidate anti-cancer agent. In other embodiments, an anti-cancer drug is selected wherein the level of a tumor cell-specific marker is increased following administration of the putative or candidate anti-tumor drug to the xenografted host non-human animal (e.g., any rodent) compared to the level of the tumor cell-specific marker prior to administration of the anti-cancer agent. In certain embodiments, the marker is a miRNA marker and the tumor is lung cancer, prostate cancer, or colon cancer.

In one aspect, a method for selecting an anti-cancer drug for treatment of a patient that has a tumor is provided, comprising introducing into a suitable mouse or host non-human animal (e.g., any rodent) a xenograft of the patient's tumor, administering a putative or candidate anti-cancer agent to the xenografted mouse or host non-human animal (e.g., any rodent), and determining the level of one or more intracellular tumor markers that have entered the mouse's circulation from a cell of the xenograft, wherein a putative or candidate anti-tumor agent that releases a predetermined level of one or more of the intracellular tumor cell markers from the cell of the xenograft is selected as a suitable therapeutic for treating the patient. Thus, as used herein the term "derived from" refers to a tumor cell, a tumor tissue, or a tumor organ taken from a human patient or propagated from a tumor cell or tumor tissue taken from a human patient.

Embodiments herein provide kits for qualifying cancer status in a subject, wherein the kits can be used to detect the differential presence of the biomarkers described herein. For example, the kits can be used to detect a differential presence of any combination of the biomarkers in tumor samples of cancer subjects before and after exposure to an anti-cancer drug or other therapeutic drug. The kits of the invention have many applications. For example, the kits can be used to monitor efficacy of a therapeutic drug in a cancer subject. The kits can also be used to identify agents useful in the treatment of cancer.

Other features and advantages of the disclosure will be apparent from the following description and from the claims.

DETAILED DESCRIPTION

Figure 1:
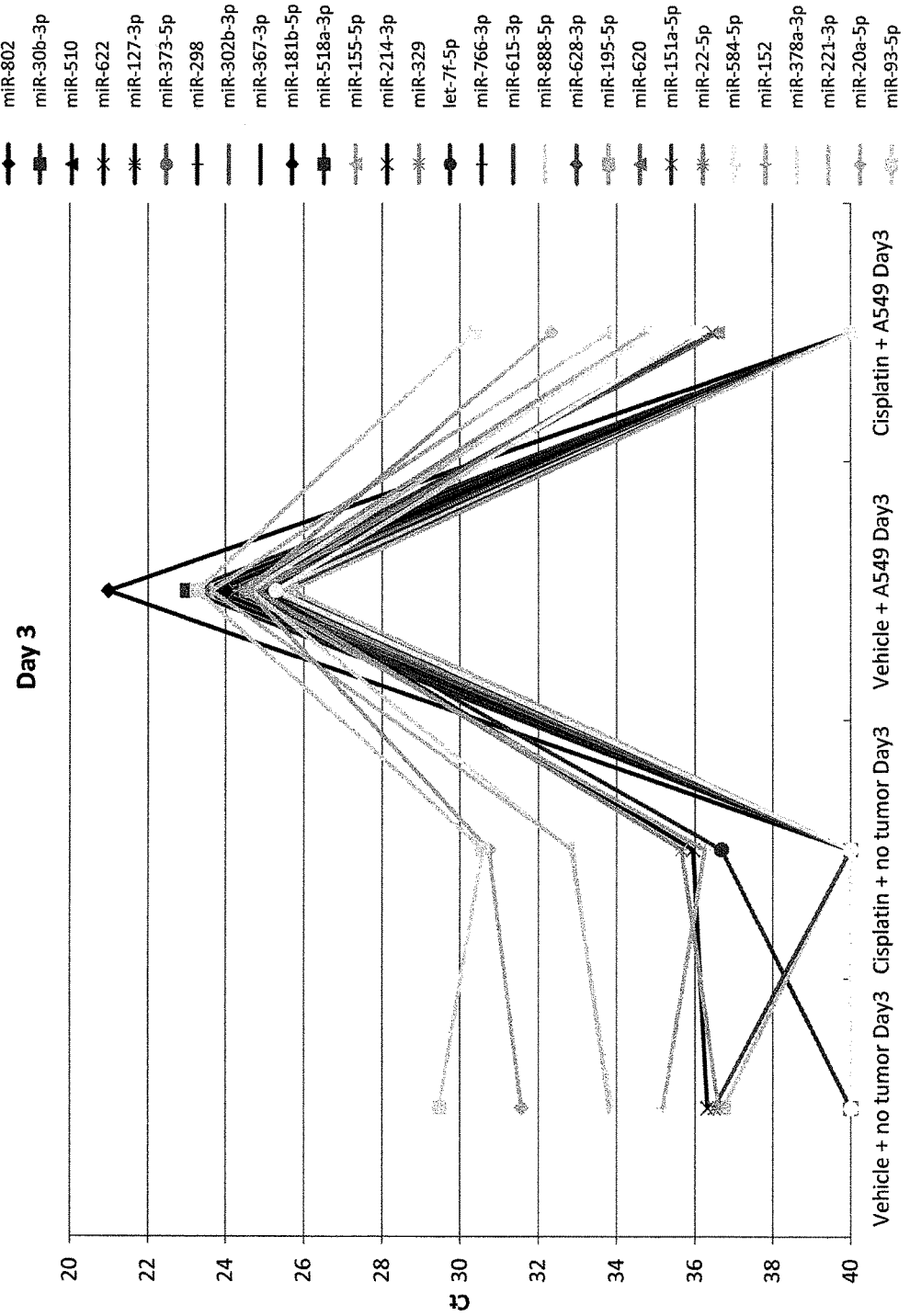
FIG. 1 shows the increase in certain miRNA markers upon A549 lung cancer tumor implantation and subsequent decrease in miRNA marker level three days following administration of the anti-tumor drug Cisplatin.
Figure 2:
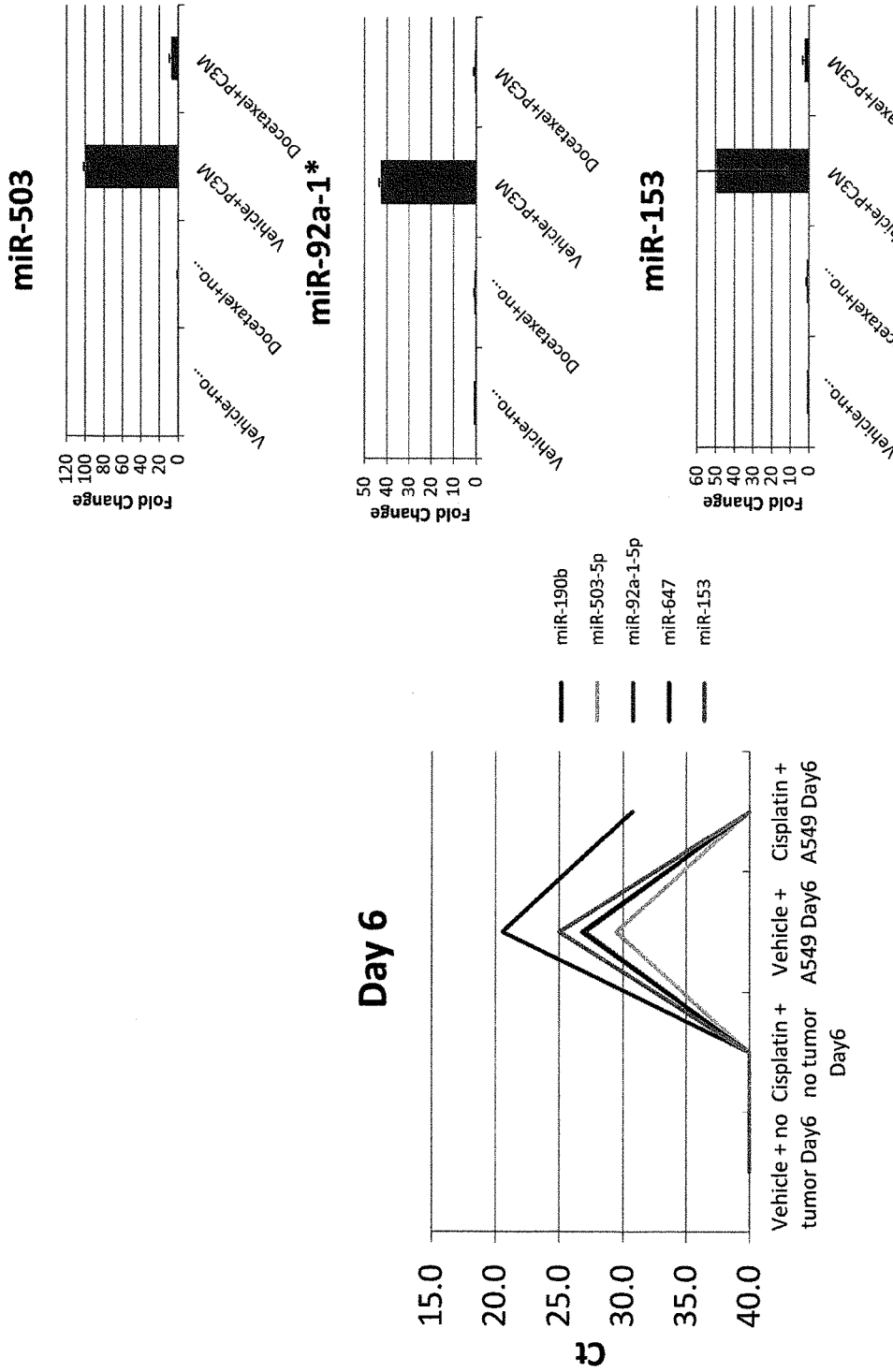
FIG. 2 shows that particular miRNA marker levels decrease upon administration of Cisplatin to lung tumors (A549) and administration of Docetaxel to prostate tumors (PC3M).
Figure 3:
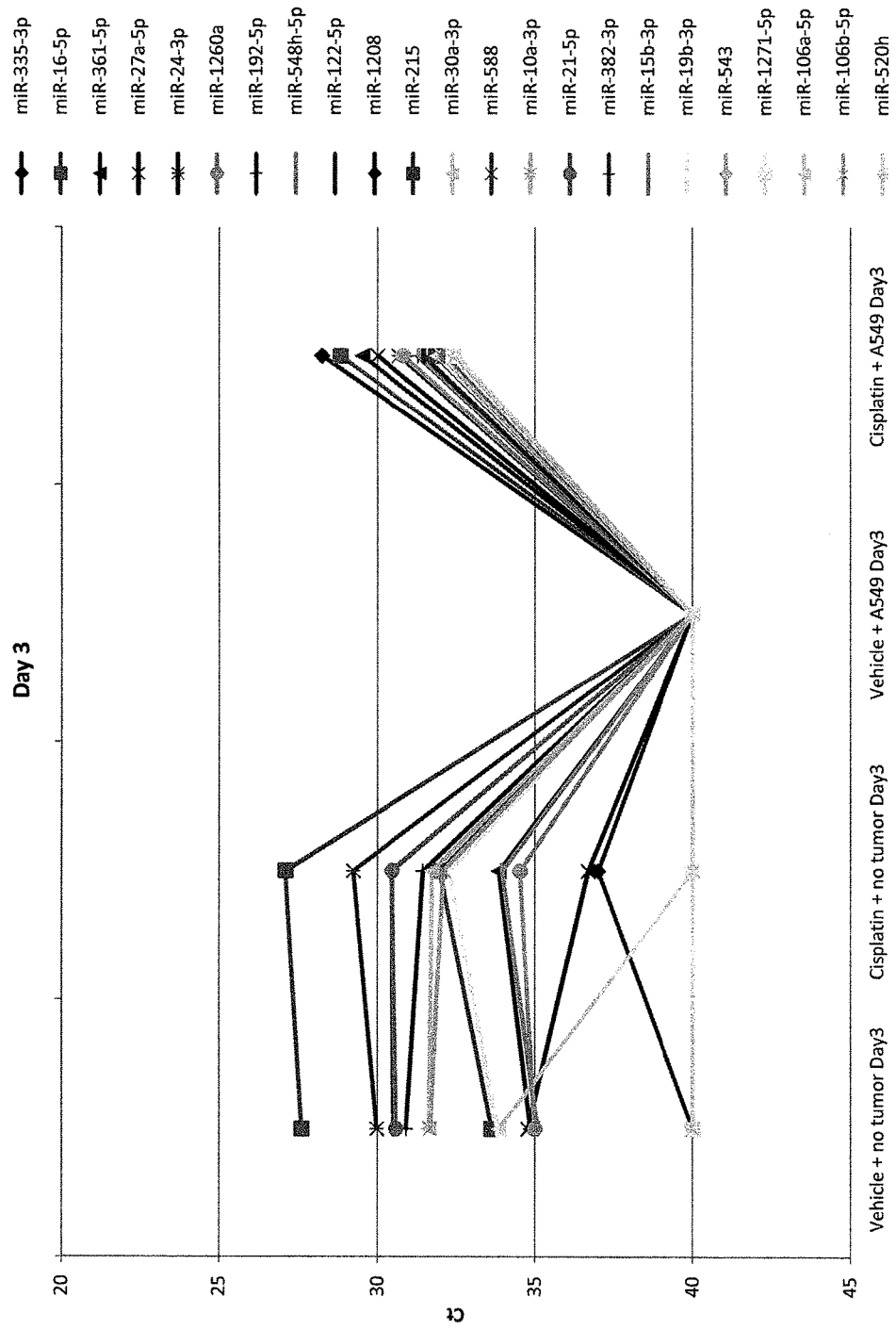
FIG. 3 shows the decrease in certain miRNA markers upon A549 lung cancer tumor implantation and subsequent increase in miRNA marker level three days following administration of the anti-tumor drug Cisplatin.
Figure 4:
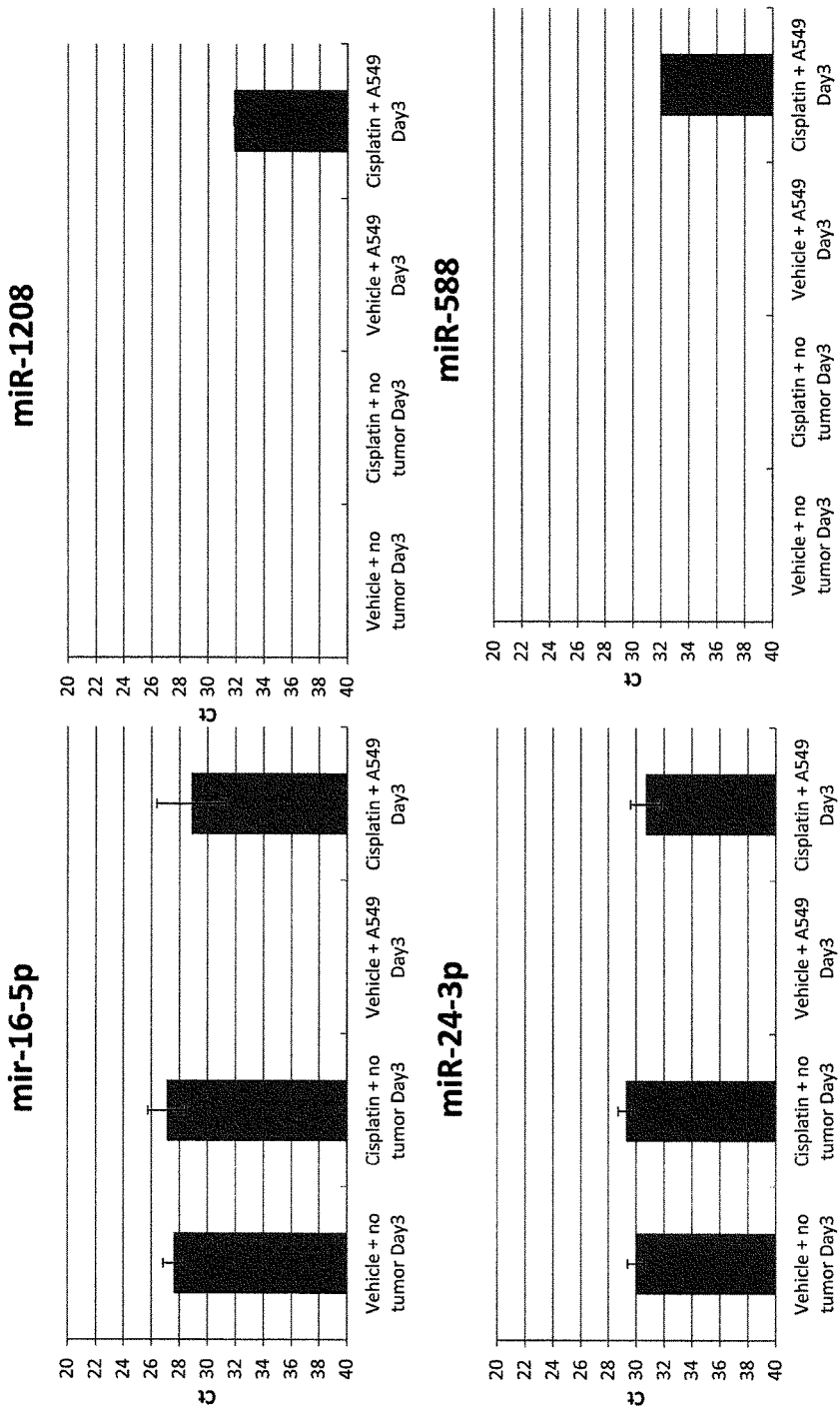
FIG. 4 shows the decrease in miR-16-5p, miR-1208, miR-24-3p, and miR-588 upon A549 lung cancer tumor implantation and subsequent increase in miRNA marker level three days following administration of the anti-tumor drug Cisplatin.
Figure 5:
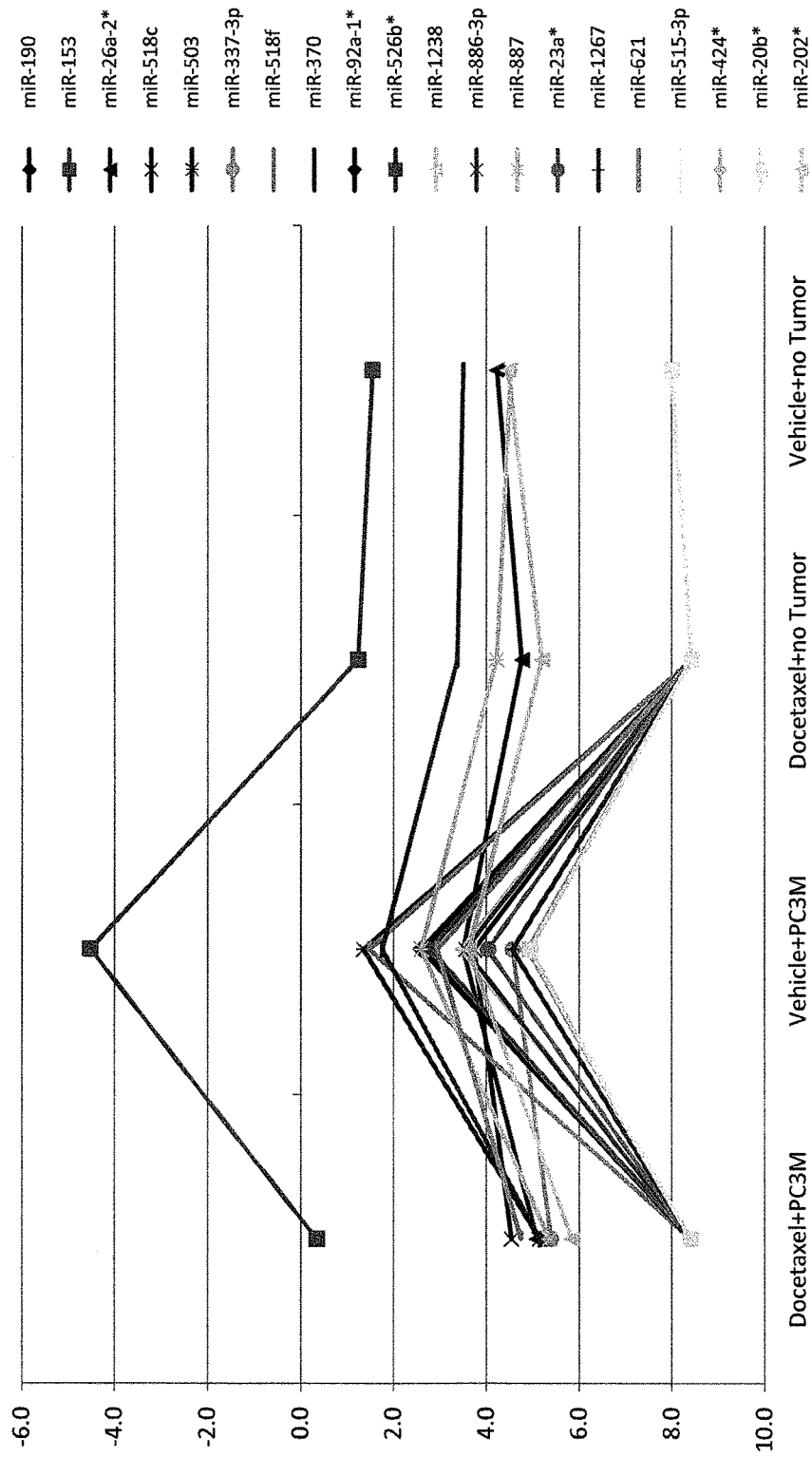
FIG. 5 shows the increase in certain miRNA markers upon PC3M prostate cancer tumor implantation and subsequent decrease in miRNA marker level following administration of the anti-tumor drug Docetaxel.
Figure 6:
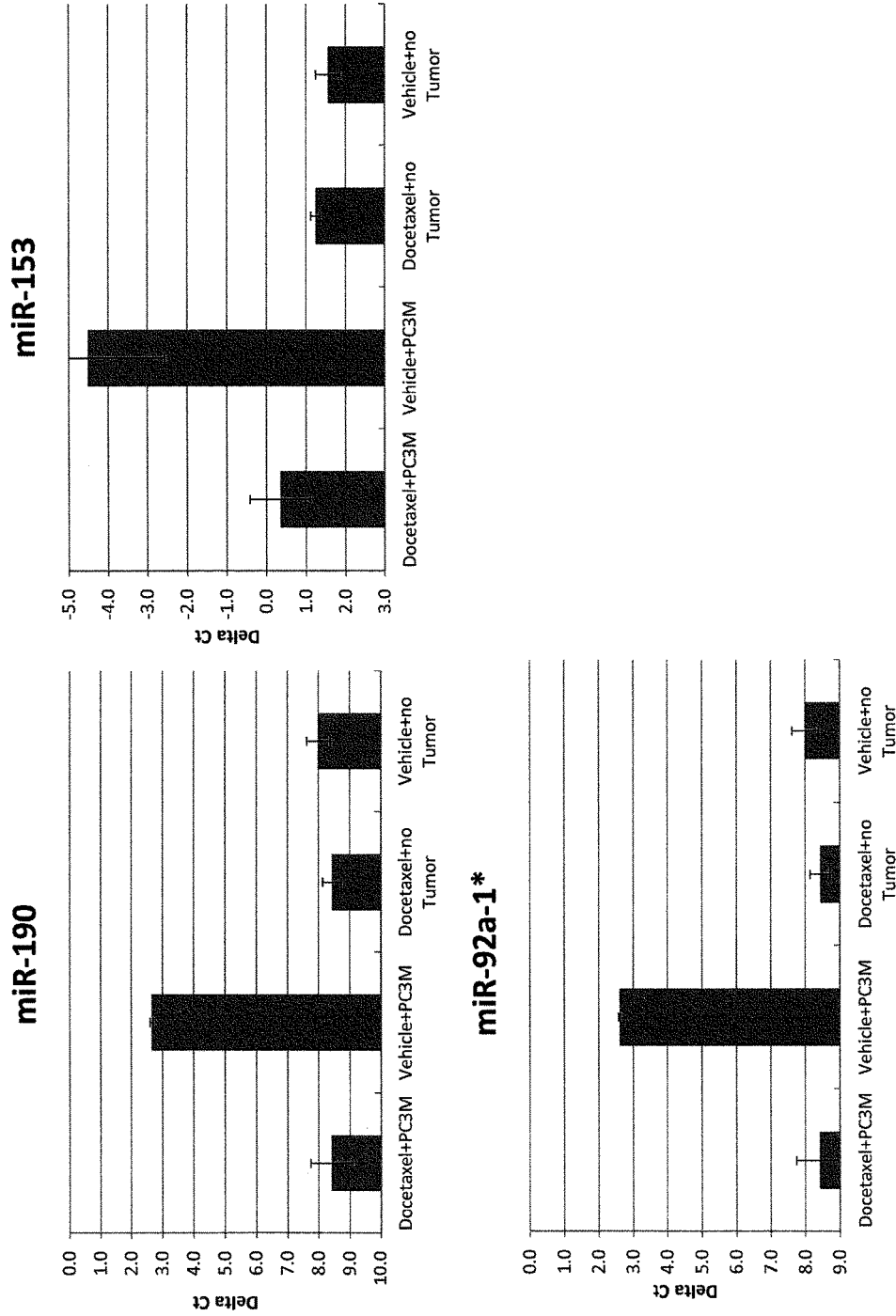
FIG. 6 shows the increase in miR-190, miR-153, and miR-92a-1 upon PC3M prostate cancer tumor implantation and subsequent decrease in miRNA marker level following administration of the anti-tumor drug Docetaxel.
Figure 7:
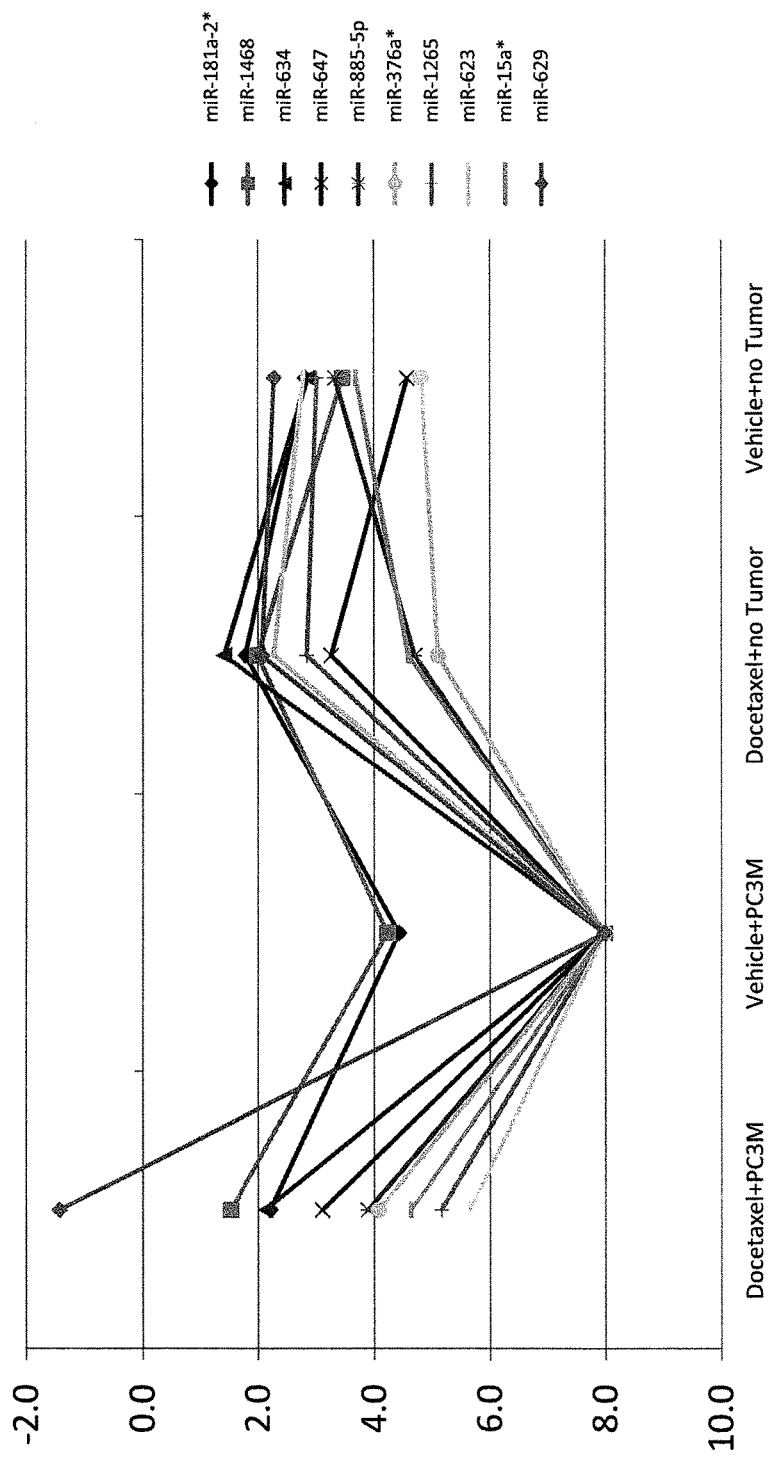
FIG. 7 shows the decrease in certain miRNA markers upon PC3M prostate cancer tumor implantation and subsequent increase in miRNA marker level following administration of the anti-tumor drug Docetaxel.
Figure 8:
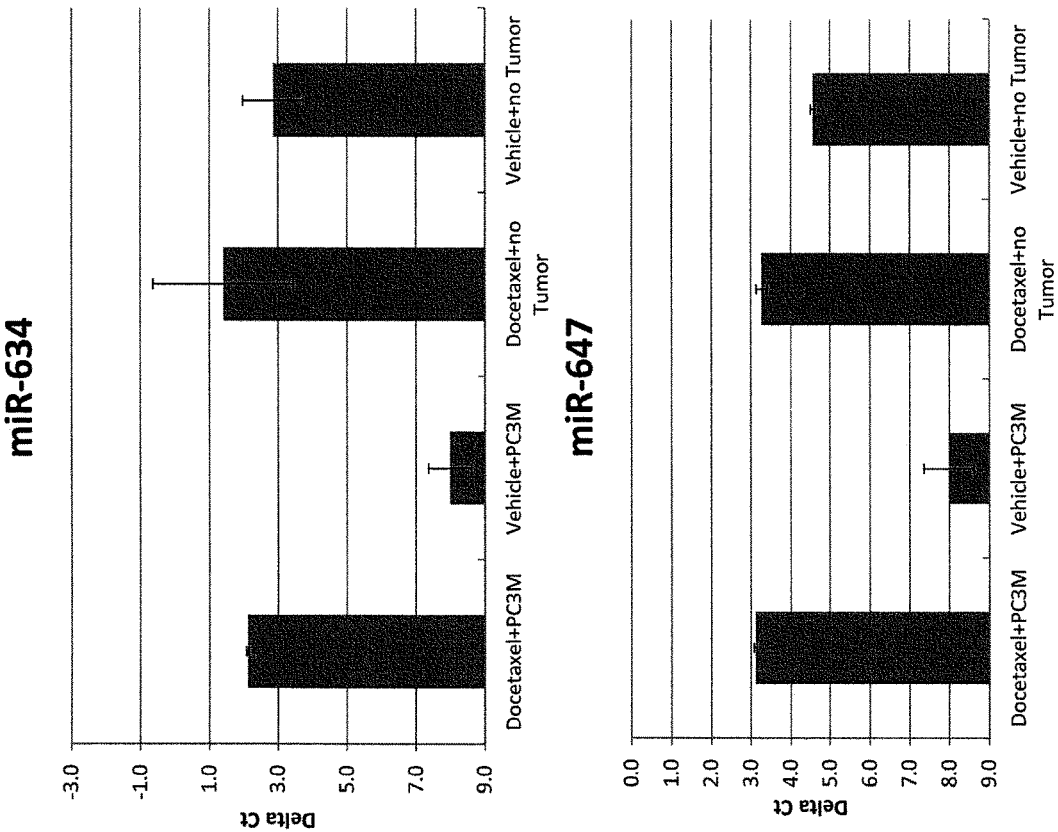
FIG. 8 shows the decrease in miR-634, and miR-647 upon PC3M prostate cancer tumor implantation and subsequent increase in miRNA marker level following administration of the anti-tumor drug Docetaxel.

Provided herein are methods, which determine cancer-killing (or tumor-killing) efficacy of an anti-cancer (or anti-tumor drug), including in a patient treated with an anti-cancer drug, methods of selecting an effective anti-cancer drug for treatment in a patient in need thereof, methods of adjusting a dosage of an anti-cancer drug for treatment of a cancer in a patient, and methods of assessing a therapeutic efficacy of an anti-cancer drug in a patient. Each of these methods is noninvasive, requiring the patient to provide samples that can be obtained from a simple blood test or from blood, plasma, serum, cerebrospinal fluid, synovial fluid, lymph, saliva, or urine obtained from a subject. These methods provide fast and accurate information to the patient and health care professional thereby providing and maximizing the usefulness of treatments reliant on anti-cancer drugs or other anti-cancer therapeutics. Methods are also provided for screening and selecting anti-cancer therapeutics for target cancers, and identifying target therapeutics most useful in treating any one particular type of cancer.

In this light, methods are disclosed, which measure the levels of certain cancer-specific biomarkers, such as microRNAs, cell free DNA (cfDNA), and other cytosolic or nuclear macromolecules normally contained within cells, but that are released from cancer cells after exposure to an anti-cancer drug; and compare the release of control markers from normal cells after exposure to the same anti-cancer drug to determine the extent and ratio of cancer cells killed relative to normal cells killed following the anti-cancer treatment. In particular embodiments, the biomarkers are tumor-responsive biomarkers that respond to changes in tumor burden but are not necessarily derived from a tumor cell, tumor tissue, or tumor organ. In some circumstances, the levels of certain biomarkers (e.g., miRNA markers) in a sample are decreased following administration of anti-cancer drug.

Before embodiments of the present invention are further described, it is to be understood that methods described herein are not limited by the recited experimental conditions; as such methods and conditions may vary. It is also to be understood that the terminology used herein is for the purpose of describing particular embodiments only, and is not intended to be limiting, since the scope of the present invention will be limited only by the appended claims.

Although any methods and materials similar or equivalent to those described herein can be used in the practice or testing of the present invention, the various embodiments of the methods and materials are now described. All patents, applications and non-patent publications mentioned in this specification are incorporated herein by reference in their entireties.

Unless defined otherwise, all technical and scientific terms used herein include the meaning commonly understood by a person skilled in the art to which this invention belongs. The following references provide one of skill with a general definition of many of the terms used in this invention: Lackie and Dow, The Dictionary of Cell & Molecular Biology (3 ed. 1999); Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

As used herein, the term "about", when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

The terms "cancer" and "cancerous" refer to or describe the physiological condition in mammals that is typically characterized by unregulated cell growth. Examples of cancer include, but are not limited to, lymphoma and leukemia, and solid tumors. By "B cell-related cancer" or "cancer of B-cell lineage" or "neoplastic B-cell growth" is intended any type of cancer in which the dysregulated or unregulated cell growth is associated with B cells.

"Tumor" as used herein, refers to all neoplastic cell growth and proliferation, whether malignant or benign, and all pre-cancerous and cancerous cells and tissues. "Neoplastic" as used herein, refers to any form of dysregulated or unregulated cell growth, whether malignant or benign, resulting in abnormal tissue growth. Thus, "neoplastic cells" include malignant and benign cells having dysregulated or unregulated cell growth. As described herein, the compositions and methods can be used for both anti-cancer and anti-tumor applications.

Cancer can be from an organ, e.g., selected from the group consisting of skin, colon, thyroid, ovarian, lung, and pancreas. In one embodiment, the skin tumor is a melanoma. In another embodiment, the tumor is selected from the group consisting of: prostate carcinoma, lung carcinoma, breast carcinoma, ovarian carcinoma, skin carcinoma, colon carcinoma, urinary bladder carcinoma, liver carcinoma, gastric carcinoma, renal cell carcinoma, nasopharyngeal carcinoma, squamous cell carcinoma, thyroid papillary carcinoma, cervical carcinoma, sarcomas, glioma, acute myelogenous leukemia, pancreatic carcinoma, and head and neck carcinomas. In yet another embodiment, the cancer is non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lympohoblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, Waldenstrom's Macroglobulinemia, mantle cell lymphoma, and heavy chain disease. In some aspects, the tumor is characterized by neoplastic B-cell growth.

The word "label" when used herein refers to a detectable compound or composition that is conjugated directly or indirectly to an antigen-binding protein or an antigen-binding fragment thereof so as to generate a "labeled" antigen-binding protein or an antigen-binding fragment thereof. The label may be detectable by itself (e.g., radioisotope labels or fluorescent labels) or, in the case of an enzymatic label, may catalyze chemical alteration of a substrate compound or composition that is detectable.

A "subject" is a vertebrate, for example, a mammal, and illustratively, a primate such as a human. Mammals include, but are not limited to, primates, (including humans), farm animals, sport animals, wildlife, and pets. A "patient" can be any subject but is typically a human. A "patient" can also refer to a plurality of patients, such as a plurality of human patients.

A "sample" or "biological sample" includes, for example, blood, plasma, serum, cerebrospinal fluid, synovial fluid, lymph, saliva, or urine obtained from a subject. A sample can be any fluid or component obtained from a subject in which the level of a cell-specific marker can be measured.

"Tumor cell-specific marker" as used herein includes a polypeptide (of a particular molecular weight) or nucleic acid, which is sequestered within a tumor cell prior to death of the tumor cell, e.g., prior to treatment with an anti-tumor drug but is released into the patient's circulation following the treatment. A "tumor cell-specific marker" also includes markers that are released by tumor cells prior to damage or death of the tumor cell (e.g., prior to treatment with an anti-tumor drug) but are maintained in the cell and not following the treatment with an anti-tumor drug. In certain embodiments, tumor cell-specific markers are miRNA markers. Polypeptide biomarkers can be identified by molecular mass in Daltons, and include the masses centered on the identified molecular masses for each marker. Nucleic acid biomarkers can be identified by sequence. "Tumor cell-specific biomarker" includes, for example, biomarkers of cellular apoptosis, cell proliferation and survival. Exemplary tumor-specific biomarkers include, but are not limited to, CD20, B lymphoid tyrosine kinase (BLK), and combinations thereof. In various aspects, cancer or tumor cells may die spontaneously, or for natural or unknown reasons, and in various embodiments a change in the level of a particular marker in response to anti-cancer or anti-tumor therapy is an indicator of efficacy or putative efficacy of the anti-cancer or anti-tumor therapy in a human.

The term "biomarker" as used herein includes, but is not limited to, a nucleic acid, peptide, protein, lipid, antigen, carbohydrate or proteoglycan, such as DNA (including, for example, cell-free DNA (cfDNA)) or RNA. The RNA can be mRNA, miRNA, snoRNA, snRNA, rRNAs, tRNAs, siRNA, hnRNA, or shRNA, or short or long non-coding RNAs. The DNA (e.g., cfDNA) or RNA (e.g., mRNA) can include point mutations, DNA hypermethylations, microsatellite instabilities, and losses of heterozygosity, or a combination thereof.

The term "tumor-responsive biomarker" as used herein includes a normal component of the serum, plasma, or other body fluid that changes in response to tumor burden but is not necessarily derived from the tumor. The tumor-responsive biomarkers may be either directly or inversely proportional to the tumor burden. That is, the level of the tumor-responsive biomarker may increase as the tumor burden decreases, or the level of the tumor-responsive biomarker may decrease as the tumor burden decreases. As used herein, the term "tumor burden" refers to the amount of tumors in a patient or non-human animal. In some embodiments a tumor-responsive biomarker includes a tumor cell-specific marker. In one embodiment, the tumor-responsive biomarker is a tumor type-specific biomarker. For example, the tumor-responsive biomarker can be specific for lung tumors, prostate tumors, or colon tumors. In one embodiment, the tumor-responsive biomarker is a tumor cell-specific biomarker. In one embodiment, the tumor-responsive biomarker is an anti-cancer drug-specific biomarker. For example, the tumor-responsive biomarker can be specific for treatments with certain types of drugs. In specific embodiments, the tumor-responsive biomarker is a miRNA marker.

Particularly useful biomarkers include those typically not secreted, e.g. mRNAs, rRNA, microRNAs, DNAs, and a combination thereof. In some embodiments, the biomarker is an intracellular biomarker, e.g., one or more intracellular proteins. In one embodiment, the intracellular proteins are cytosolic protein. In one embodiment, the biomarker is a transmembrane or membrane-associated protein. In one embodiment, the intracellular proteins are organellar proteins residing in or associated with an organelle. In one embodiment, the intracellular proteins are nuclear proteins. In certain embodiments, useful biomarkers for the methods disclosed herein are released by tumor cells into the extracellular space, into the blood, or any other area surrounding the cells prior to treatment with an effective anti-tumor drug, but are not released following administration of the anti-tumor drug.

"Non-specific" or "control" marker can be a general marker of cell toxicity, markers, which are not specific to tumor cells.

The term "measuring" includes methods, which include determining, detecting, or observing the presence or absence of marker(s) in the sample, quantifying the amount of marker(s) in the sample, and/or qualifying the type of biomarker (e.g., measuring epigenetic changes, sequence changes, etc.). Measuring can be accomplished by methods known in the art and those further described herein. Any suitable methods can be used to detect and measure one or more of the markers described herein. These methods include, without limitation, immunoassays, mass spectrometry (e.g., laser desorption/ionization mass spectrometry, SELDI), fluorescence (e.g., sandwich immunoassay), surface plasmon resonance, ellipsometry, atomic force microscopy, PCR (including quantitative PCR, e.g., real-time PCR), and microarray analysis (for example, with Significance Analysis of Microarrays (SAM) software). In one embodiment, microarray analysis is used to detect microRNA, known as microRNA or miRNA expression profiling.

In some embodiments, a difference in the amount of the tumor cell-specific marker in the sample as compared to a control or baseline indicates that the putative anti-tumor drug has a therapeutic efficacy. For example, an increase (e.g., a one-fold, a two-fold, a three-fold, a four-fold, a five-fold, a six-fold, a seven-fold, an eight-fold, a nine-fold, or a ten-fold or more increase) in the amount of a marker in the sample as compared to the control indicates that the putative anti-tumor drug has efficacy. That is, the change in the amount of the tumor cell-specific marker in the sample can be at least one fold (e.g., a two-fold, a three-fold, a four-fold, a five-fold, a six-fold, a seven-fold, an eight-fold, a nine-fold, or a ten-fold or more) higher than the change in the amount of control marker. In some embodiments, the change in the amount of the tumor cell-specific marker in the sample can be at least one fold (e.g., a two-fold, a three-fold, a four-fold, a five-fold, a six-fold, a seven-fold, an eight-fold, a nine-fold, or a ten-fold or more) lower than the change in the amount of control marker. In certain embodiments, the marker is a tumor-responsive biomarker.

The change in the amount of the tumor-responsive biomarker can be at least one fold, at least two fold, at least three fold, at least four fold, at least five fold, at least six fold, at least seven fold, at least eight fold, at least nine fold, at least ten fold or more in a sample obtained before administration of an anti-tumor drug compared to a sample obtained after administration of an anti-tumor drug. The change in the amount of tumor-responsive biomarker before and after the administration of an anti-tumor drug can be an increase or a decrease.

In certain embodiments, an increase (e.g., a one-fold, a two-fold, a three-fold, a four-fold, a five-fold, a six-fold, a seven-fold, an eight-fold, a nine-fold, or a ten-fold or more increase) in the amount of a biomarker after administration of an anti-tumor drug as compared to the amount of a biomarker before anti-tumor drug administration indicates that the putative anti-tumor drug has efficacy. In other embodiments, a decrease, (e.g., a one-fold, a two-fold, a three-fold, a four-fold, a five-fold, a six-fold, a seven-fold, an eight-fold, a nine-fold, or a ten-fold or more decrease) in the amount of a biomarker after administration of an anti-tumor drug as compared to the amount of a biomarker before anti-tumor drug administration indicates that the putative anti-tumor drug has efficacy. Likewise, depending on the selected marker, absence of an increase or an absence of a decrease in the level of a tumor-responsive biomarker after administration of an anti-tumor drug can indicate that the administration of the anti-cancer drug was not therapeutically effective.

While embodiments described herein reflect fold increases over the control, it is further contemplated that certain markers such as tumor suppressor markers or anti-apoptotic markers may show fold decreases relative to the amount of control marker. For example, a decrease (e.g., a one-fold, a two-fold, a three-fold, a four-fold, a five-fold, a six-fold, a seven-fold, an eight-fold, a nine-fold, or a ten-fold or more decrease) in the amount of a marker in the sample as compared the amount of control marker can indicate that the putative anti-tumor drug has efficacy. That is, the decreased amount of the marker peptide in the sample can be at least one fold (e.g., a two-fold, a three-fold, a four-fold, a five-fold, a six-fold, a seven-fold, an eight-fold, a nine-fold, or a ten-fold or more) lower than the decrease of the amount of control marker.

"Detect" includes identifying the presence, absence or amount of the object to be detected.

The terms "polypeptide", "peptide", and "protein" are used interchangeably herein to include a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide", "peptide" and "protein" include glycoproteins, as well as non-glycoproteins.

While the methods described herein are specific to cancer and tumors, it is contemplated herein that the methods are also useful in other disease states, including, for example, multiple sclerosis and other autoimmune diseases.

Methods

In various aspects, provided herein are noninvasive methods for determining tumor cell-killing efficacy in a patient treated with an anti-tumor drug. In some embodiments, the methods comprise measuring a blood level of an intracellular tumor cell-specific marker in the patient following administration of a putative anti-tumor drug. An increase in the level of the intracellular tumor cell-specific marker for example, in the blood, plasma, serum, cerebrospinal fluid, synovial fluid, lymph, saliva, or urine of the patient compared to a control marker is indicative of efficacy of the putative anti-tumor drug. In some embodiments, a change in the level of a tumor-cell specific marker after administration of a putative anti-tumor drug is indicative of efficacy of the putative anti-tumor drug. Such a change can be an increase or a decrease in the level of a tumor-cell specific marker. In specific embodiments, a change in the level of at least one tumor-responsive biomarker before and after administration of an anti-tumor drug correlates to reduction in the size, severity, and/or prevalence of cancer cells in the patient.

The patient can be treated with the putative anti-tumor drug if the level of intracellular tumor cell-specific marker increases following administration of the putative anti-tumor drug, particularly if the increase is relative to the control marker. Patients can also be treated with the putative anti-tumor drug if the level of intracellular tumor cell-specific marker decreases following administration of the putative anti-tumor drug, and/or if the decrease is relative to the control marker. In some embodiments the marker used for determining drug efficacy is a tumor-responsive biomarker. In some embodiments, the anti-tumor drug is an anti-tumor drug conjugate of an antigen-binding protein and a drug, the tumor cell-specific marker is a cancer-specific marker, and the cancer is a solid tumor or a B-cell related cancer. For example, in certain embodiments, the cancer is prostate, lung, or colon cancer and the marker is a miRNA marker.

As noted throughout, any of the methods described herein can comprise one or more further steps of obtaining levels of a second marker, e.g., a control (general) cell marker or non-specific marker, which when present in a sample or in circulation indicates damage to normal cells. Thus, the release of control cell markers from normal cells after exposure to an anti-cancer drug will indicate the level of damage the anti-cancer drug causes to normal tissue and can, in some aspects, be used to provide a therapeutic efficacy of the drug on the tumor relative to the toxicity of the drug to normal tissue.

Also provided are methods of selecting an effective anti-tumor drug for treatment of a patient in need thereof. In some embodiments, the methods comprise measuring a first level of a tumor cell-specific marker in a first sample from a tumor-bearing patient, administering a putative anti-tumor drug to the patient, and measuring a second level of the tumor cell-specific marker in a second sample from the patient. In certain embodiments, the marker is a tumor-responsive biomarker. An increase in the second level indicates anti-tumor efficacy of the putative anti-tumor drug and the patient is treated with the putative anti-tumor drug, thereby selecting an effective anti-tumor drug for treatment of the patient. A decrease in the second level may also indicate efficacy of the putative anti-tumor drug. Likewise, the absence of an increase or the absence of a decrease in the level of a tumor-responsive biomarker can indicate that the administration of the anti-tumor drug is not therapeutically effective. In some embodiments the selection of a tumor cell-specific marker will determine whether an increase or decrease in the level of tumor cell-specific marker following administration of anti-tumor drug is indicative of anti-tumor efficacy of the administered drug. In some embodiments, the anti-tumor drug is an anti-cancer drug, the tumor cell-specific marker is a cancer-specific marker, and the tumor-bearing patient is a cancer-bearing patient.

Further provided are methods of adjusting or controlling a dosage of an anti-tumor drug for treatment of a tumor in a patient. In some embodiments, the methods comprise measuring a level of one or more tumor cell-specific markers in the circulation of a patient who has been administered an initial amount of the anti-tumor drug, and adjusting the dosage for subsequent administration of the anti-tumor drug to the patient based upon the level of the one or more tumor cell-specific markers in the circulation of the patient after administration of the initial amount of the anti-tumor drug. In some embodiments, the anti-tumor drug is an anti-cancer drug, and the tumor cell-specific marker is a cancer-specific marker or a tumor-responsive biomarker.

For example, in some embodiments, the dosing regimen of anti-tumor drug administered to patients is changed when the level of a tumor-responsive biomarker after the first dose of the anti-tumor drug does not increase compared to the level of the tumor-responsive biomarker prior to administration of the anti-tumor drug. In specific embodiments, the dosing regimen of the anti-tumor drug is changed when the level of at least one miRNA marker including miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-647, miR-885-5p, miR-376a, miR-1265, miR-623, miR-15a, miR-629, miR-30d-3p, miR-483-5p, miR-708-3p, and a combination thereof, is not increased after administration of an anti-tumor drug compared to prior to anti-tumor drug administration.

In some embodiments, the dosing regimen of anti-tumor drug administered to a patient is changed when the level of the tumor-responsive biomarker after the first dose of the anti-tumor drug does not decrease compared to the level of the tumor-responsive biomarker prior to administration of the anti-tumor drug. In specific embodiments, the dosing regimen of the anti-tumor drug is changed when the level of at least one miRNA marker including miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, and a combination thereof, is not decreased after administration of an anti-tumor drug compared to prior to anti-tumor drug administration.

Depending on the outcome of the comparison of tumor-responsive biomarker level prior to and following anti-tumor drug administration, different patients may receive different second or subsequent dosages of anti-tumor drug. As used herein, an alteration or adjustment in the dosage regimen of an anti-tumor drug can be an increase in the dosage or a decrease in the dosage of the anti-tumor drug. For example, an increase or decrease in the dosage of an anti-tumor drug could be an increase or decrease in the amount, concentration, duration, or frequency of the anti-tumor drug administration.

According to certain embodiments of the present invention, multiple doses of an anti-tumor drug may be administered to a subject over a defined time course. Such methods can comprise sequentially administering to a subject multiple doses of an anti-tumor drug. As used herein, "sequentially administering" means that each dose of anti-tumor drug is administered to the subject at a different point in time, e.g., on different days separated by a predetermined interval (e.g., hours, days, weeks or months). The present disclosure includes methods which comprise sequentially administering to the patient a single initial dose of an anti-tumor drug, followed by one or more subsequent doses of the anti-tumor drug depending on the relative level of at least one tumor-responsive biomarker before and after administration of the first or a subsequent dosage of the anti-tumor drug.

The terms "initial dose," and "subsequent dose," refer to the temporal sequence of administration of the anti-tumor drug. Thus, the "initial dose" or "first dose" is the dose which is administered at the beginning of the treatment regimen; the "second dose" or "subsequent dose" is the dose which is administered after the initial dose. The initial and subsequent doses may all contain the same amount of anti-tumor drug, but generally may differ from one another in terms of frequency of administration. In certain embodiments, however, the amount anti-tumor drug contained in the initial and subsequent doses varies from one another (e.g., adjusted up or down as appropriate) during the course of treatment depending on the relative levels of at least one tumor-responsive biomarker before and after administration of the anti-tumor drug.

As used herein, the term "dosage regimen" refers to a drug administration decision regarding formulation, route of administration, drug dose, dosing interval and treatment duration. Thus, if a dosage regimen of an anti-tumor drug is changed in response to an increase or decrease in the level of at least tumor cell-specific marker following administration of the anti-tumor drug, the formulation, route of administration, drug dose, dosing interval, or treatment duration can be changed. For example, if the level of a tumor cell-specific marker following administration of a dose of an anti-tumor drug does not indicate that the dose was therapeutically effective, the dosage regimen can be changed to increase the frequency, concentration, level, route of administration, or duration of treatment of the anti-tumor drug. In certain embodiments, changing the dosage regimen of the anti-drug increases the therapeutic efficacy of the anti-tumor drug.

In one embodiment, subsequent doses can be administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 1½, 14, 14½, 15, 15½, 16, 16½, 17, 17½, 18, 18½, 19, 19½, 20, 20½, 21, 2½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-tumor drug which is administered to a patient prior to the administration of the very next dose in the sequence with no intervening doses.

The methods disclosed herein can comprise administering to a patient any number of secondary or subsequent doses of an anti-tumor drug. For example, in certain embodiments, only a single second dose is administered to the patient. In other embodiments, two or more (e.g., 2, 3, 4, 5, 6, 7, 8, or more) subsequent doses are administered to the patient.

In embodiments involving multiple second or subsequent doses, each dose may be administered at the same frequency or altered frequency as the other doses depending on the relative level of a tumor cell-specific marker. For example, each subsequent dose may be administered to the patient 1 to 2 weeks after the immediately preceding dose. The frequency at which subsequent doses are administered to a patient can vary over the course of the treatment regimen. The frequency of administration may also be adjusted during the course of treatment by a physician depending on the needs of the individual patient following clinical examination or based on the relative levels of at least one tumor-responsive biomarker following administration of each dose.

Accordingly, the level of a tumor cell-specific marker can be monitored during multiple administrations of an anti-tumor drug in order determine the therapeutic efficacy of the anti-tumor drug throughout the course of administration. Following each dose, the concentration, level, duration, and/or frequency of anti-tumor drug administration can be altered based on the level of a tumor-responsive biomarker (e.g., a miRNA marker) following each administration of the anti-tumor drug relative to the level of the tumor-responsive biomarker prior to each dose of the anti-tumor drug.

The dosage regimen of an anti-tumor drug can be increased or decreased in patients having a marker comparison that does not indicate therapeutic efficacy of an anti-tumor drug. For example, if the marker comparison indicates that the anti-tumor drug was not therapeutically effective, the patient can receive a second or subsequent dose that is the same or greater than the first dosage of anti-tumor drug. An increase in the second or subsequent dose can be a change in the dosage regimen such that the anti-tumor drug is delivered more frequently, in a greater amount, or for a longer time than the previous dose. For example, an increase in the second or subsequent dose can be a decrease in the amount of time between doses, or an increase in the amount or concentration of the dose of anti-tumor drug. For example, the second or subsequent dose can be increased by a factor of at least 1, at least 1.5, at least 2, at least 3, at least 4, at least 5, at least 10, at least 20 or more. The second or subsequent dose can be administered in combination with another anti-tumor drug or any other therapeutic composition.

Likewise, the dosage regimen of patients having a marker comparison that indicates efficacy of an anti-tumor drug, can be altered or maintained the same. In some embodiments, the dosage regimen can be decreased. For example, the second dosage can be decreased by a factor of at least 1.5, at least 2, at least 3, at least 4, at least 5, at least 10, at least 20 or more. A decrease in the second or subsequent dose can be an increase in the amount of time between doses, or a decrease in the amount or concentration of the dose. In certain embodiments, the anti-tumor drug is not administered in a second dose. For example, the second dosage of the anti-tumor drug can include only different anti-tumor drugs compared to the first dosage.

In some embodiments, the dosage of an anti-tumor drug can be altered based on any medically appropriate reason or based on the relative levels of multiple tumor-responsive biomarkers before and after administration of an anti-tumor drug. Accordingly, the second or subsequent dosage of anti-tumor drug can be increased or decreased on average in a patient population depending on the relative level of at least one tumor-responsive biomarker before and after administration of an anti-tumor drug. Due to variations in genetics, patient characteristics, environment, and disease subtype between individual patients, a regime that is effective in one patient may not be effective in another patient or may be effective to different extents. Within a patient population, at least one patient can be administered a lower second dose than the first dose of an anti-tumor drug, at least one patient can be administered a higher second dose than the first dose of an anti-tumor drug, and at least one patient can be administered a second dose that is the same as the first dose of an anti-tumor drug.

Still further provided are methods for assessing a therapeutic efficacy of an anti-tumor drug in a patient. In some embodiments, the methods comprise (a) obtaining a first baseline sample from the patient's circulation, wherein the patient has a tumor; (b) administering to the patient a dose of an anti-tumor drug, wherein at least one tumor cell-specific marker is sequestered within the tumor cell of the patient prior to administration of the anti-tumor drug but is released into the patient's circulation following administration of the anti-tumor drug; (c) obtaining a second sample from the patient's circulation; (d) measuring an amount of the at least one tumor cell-specific marker (i) in the first baseline sample and (ii) in the second sample, and (e) comparing the amount of the tumor cell-specific marker in the first baseline sample with the amount of the tumor cell-specific marker in the second sample. An increase in the amount of the at least one tumor cell-specific marker in the second sample relative to the amount of the at least one tumor cell-specific marker in the first baseline sample is indicative of increased tumor cell death in the patient. In certain embodiments the marker is a tumor-responsive biomarker whose level changes in response to tumor burden but is not necessarily derived from a tumor. In some embodiments, a biomarker is selected such that a decrease in the amount of the tumor cell-specific marker in the second sample relative to the amount of the biomarker in the first baseline sample is indicative of increased tumor cell death. The patient can be treated with the anti-tumor drug that increases the at least one tumor cell-specific marker. Alternatively, patients can be treated with the anti-tumor drug that decreases the level of the at least one biomarker.

In some embodiments, the anti-tumor drug is an anti-cancer drug, and the tumor cell-specific marker is a cancer-specific marker. In some embodiments, a single dose of the anti-tumor drug is administered to the patient. In other embodiments, multiple doses of the anti-tumor drug are administered to the patient. Accordingly, the level of a biomarker can be determined following administration of multiple doses of an anti-tumor drug in order to monitor the effectiveness of administration of the anti-tumor drug throughout administration. In particular embodiments, the biomarker is a tumor-responsive biomarker.

It is also contemplated that embodiments herein can be used to identify anti-cancer drugs and anti-tumor drugs with high efficacy on particular types of cancer or tumors. In particular, a subject, typically a mouse or other like rodent having a pre-determined form of cancer, is tested for a baseline level of one or more biomolecules associated with the pre-determined form of cancer, e.g., a CD20 marker for lymphoma or a miRNA. The proposed anti-cancer drug for the pre-determined form of cancer is administered to the subject and the level of the biomolecule determined. Increases or decreases of the biomolecule compared to control markers are used to identify anti-cancer drugs with greater potency for killing or damaging the pre-determined form of cancer in the subject. It is contemplated that a plurality of anti-cancer drugs can be tested using this method to identify and screen for anti-cancer drugs having enhanced efficacy for various forms of cancer. In addition, anti-cancer drugs having greater efficacy for one type of cancer over another type of cancer can also be identified, thereby maximizing cancer cell killing and damage, for any one anti-cancer drug or therapeutic.

Anti-tumor drugs selected by the methods disclosed herein can be formulated into a composition for administration to a patient, such as a pharmaceutical composition. In certain embodiments, the present disclosure provides a pharmaceutical composition comprising one or more selected anti-tumor drugs as disclosed herein formulated together with a pharmaceutically acceptable carrier. The composition may optionally contain one or more additional pharmaceutically active ingredients, such as another anti-tumor drug. The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference. The pharmaceutical composition can be formulated to be suitable for intravenous, intramuscular, subcutaneous, parenteral, spinal or epidermal administration (e.g., by injection or infusion).

Also provided herein are methods which measure the levels of certain tumor-specific biomarkers, and tumor-responsive biomarkers such as mRNA, rRNA, microRNAs, cell-free DNA (cfDNA), and other cytosolic, organellar or nuclear macromolecules normally contained within cells, released from specific classes of cancer cell, or from normal cells upon development of a tumor or in the presence of a tumor, after exposure to an anti-tumor drug compared to release of similar markers from normal cells after exposure to the same anti-tumor drug, to determine the extent and ratio of tumor cells killed relative to normal cells killed following the treatment with the anti-tumor drug, i.e. therapeutic efficacy. In some embodiments, the release of certain biomarkers such as certain miRNAs is decreased after exposure to an anti-tumor drug such that therapeutic efficacy of the anti-tumor drug is found when the level of extracellular miRNA decreases after administration of the anti-tumor drug. In other embodiments, the marker is a tumor-responsive biomarker that is a normal component of the serum, plasma or other body fluid that changes in response to tumor burden but is not necessarily derived from the tumor. The tumor-responsive biomarkers may be either directly or inversely proportional to the tumor burden.

The biomarkers described herein are useful in methods for identifying the efficacy of a therapeutic drug in a cancer subject, i.e. the therapeutic efficacy or therapeutic index. The level of one or more biomarkers in a patient that has been treated with an anti-cancer drug can be determined, and the differential presence of the biomarker can be indicative of the efficacy of the treatment. For example, the differential presence of a miRNA before and after administration of an anti-tumor drug to a human subject or non-human animal can be indicative of the efficacy of the treatment with an anti-tumor drug.

Therapeutic agents (e.g. anti-tumor or anti-cancer drugs) useful in cancer treatment for a given subject may be identified using methods employing the biomarkers delineated herein. For example, a patient or other subject with cancer may be treated with an anti-cancer drug to determine the therapeutic index of that anti-cancer drug in that patient. The term "efficacy", "drug efficacy", "anti-tumor efficacy", or "therapeutic efficacy" refers to the ability of an anti-tumor drug to slow growth, prevent growth, kill, or damage tumor cells. The therapeutic efficacy is determined by measuring the amount of one or more biomarkers (e.g. a tumor specific biomarker and a non-specific biomarker or a tumor-responsive biomarker) present in a biological sample prior to treatment with the anti-cancer drug and measuring the same one or more biomarkers after treatment with the anti-cancer drug. The differential presence of the one or more biomarkers in the subject indicates that the anti-cancer drug may be a useful therapeutic in that subject, i.e. the therapeutic index is acceptable for the subject given the type and stage of the cancer, etc.

In specific embodiments, the relative level of a tumor-responsive biomarker marker can correlate to therapeutic efficacy of the anti-tumor drug. Thus, disclosed herein are methods for predicting the therapeutic efficacy of administering an anti-tumor drug by determining the relative level of at least one tumor-responsive biomarker marker before and after administering a dose of the anti-tumor drug, wherein a change in the level of the tumor-responsive biomarker correlates to the ability of an anti-tumor drug to slow growth, prevent growth, kill, or damage tumor cells. Therapeutic efficacy can be determined following a single dose, or following at least 2, at least 3, at least 4, at least 5, at least 6, at least 7, at least 8, at least 9, at least 10 or more doses of the anti-tumor drug.

In certain embodiments, determining the relative level of a tumor-responsive biomarker (e.g., a miRNA marker) before and after administration of a putative anti-tumor drug can predict the efficacy of the putative anti-tumor drug prior to traditional non-invasive techniques (e.g., CT scan, MRI scan, PET scan). Accordingly, as used herein, the term "predictive efficacy" refers to selecting a drug based on the relative level of a tumor-responsive biomarker before and after administration of a putative anti-tumor drug, before efficacy of the drug could be determined by imaging techniques such as CT scan, MRI scan, and PET scan.

In some embodiments, the anti-tumor drug is an antigen-binding protein or an antigen-binding fragment thereof. In some embodiments, the antigen-binding protein is a bispecific antigen-binding protein or an antigen-binding fragment thereof. In some embodiments, the anti-tumor drug is a conjugate of an antigen-binding protein and a drug.

Anti-tumor drugs that can be used in the methods disclosed herein include, but are not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, Leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon. In certain embodiments, cisplatin is used to treat lung cancer tumors, docetaxel is used to treat prostate cancer tumors, and irinotecan is used to treat colon cancer tumors.

Methods for determining tumor-killing efficacy in a patient (e.g., a mammal such as a human) can include the step of detecting one or both of the presence and amount (or measuring the amount) of one or more tumor cell-specific markers in a sample from a patient. In some embodiments, the presence or amount of the tumor cell-specific marker in the sample is an indication that the putative anti-tumor drug has efficacy. In some embodiments, methods for determining tumor-killing efficacy can include the step of determining the level of at least one tumor-responsive biomarker before and after administration of an anti-tumor drug. Depending on the tumor-responsive biomarker selected, increases or decreases in the level of tumor-responsive biomarker following drug administration can be indicative of efficacy.

In some embodiments, the presence of one or more tumor cell-specific markers in a sample from a patient is an indication that the putative anti-tumor drug has efficacy.

In some embodiments, a difference in the amount of one or more tumor cell-specific markers in a sample from a patient as compared to a baseline amount of the marker indicates that the putative anti-tumor drug has efficacy. An increase (e.g., a one-fold, a two-fold, a three-fold, a four-fold, a five-fold, a six-fold, a seven-fold, an eight-fold, a nine-fold, or a ten-fold or more increase) in the amount of a tumor cell-specific marker in the sample as compared to a baseline amount of the marker can be an indication that the putative anti-tumor drug has efficacy. Similarly, a decrease (e.g., a one-fold, a two-fold, a three-fold, a four-fold, a five-fold, a six-fold, a seven-fold, an eight-fold, a nine-fold, or a ten-fold or more decrease) in the amount of a biomarker in the sample as compared to a baseline amount of the biomarker can be an indication that the putative anti-tumor drug has efficacy. Likewise, the absence of an increase or the absence of an increase in the level of a tumor-responsive biomarker in the sample as compared to a baseline amount of the marker can be an indication that the administration of the putative anti-tumor drug does not have efficacy.

A baseline amount (e.g., an amount or level obtained from a patient prior to treatment with the putative anti-tumor drug or an amount or level obtained from one or more subjects prior to treatment with any anti-tumor drug) can be determined using any of a variety of well-known methods. For example, samples from a group of individuals known to have a given cancer can contain, on average, an amount X of a tumor cell-specific marker prior to treatment with any anti-tumor drug, whereas samples from a group of individuals after treatment with a given anti-tumor drug can contain, on average, an amount of a tumor cell-specific marker that is on average two-fold higher than X or two-fold lower than X. In some embodiments, the baseline amount is determine based on a tumor-responsive biomarker.

The methods disclosed herein can be performed by a single party or by separate parties. For example, the party determining the level of a tumor-responsive biomarker can be different than the party administering the first and subsequent dosages of anti-tumor drug. In some embodiments, the party that determines the level of the tumor-responsive biomarker is the same party that administers the dosages of the anti-tumor drug.

Sample Collection

Biological samples can be collected from a subject using any acceptable procedure in the art, for example, by needle aspiration of bodily fluids, removal of a tissue sample (e.g., biopsy, for example, fine needle aspiration biopsy, core needle biopsy, or excisional biopsy), and the like. Typical collection is noninvasive in nature utilizing easily assessable fluids. However, samples can be obtained from, for example, blood, plasma, serum, cerebrospinal fluid, synovial fluid, lymph, saliva, or urine from a subject. In certain embodiments, the samples are blood samples extracted or drawn from an individual or group of individuals by any conventional method. The blood may be drawn from a vein or an artery of an individual or group of individuals. Where a biological sample must be stored prior to assay, the biological sample can be transferred to a glass slide prior to assay or may be frozen for later preparation or immediately placed in a fixative solution. The sample extracted from an individual by any means as disclosed above may be transferred to a tube or container prior to analysis. The container may be empty, or may comprise a collection media of sorts.

Samples can be collected any time prior to administration of an anti-tumor drug and following administration of an anti-tumor drug. For example, samples can be collected immediately before, 6 hours before, 12 hours before, 1 day before, 2 days before, 3 days before, 4 days before, 5 days before, 6 days before, 8 days before, 10 days before, two weeks before, one month before, 1-3 months before, 3-6 months before, 6-12 months before, or longer before administration of an anti-tumor drug. Samples can also be collected from the patient immediately after, 6 hours after, 12 hours after, 1 day after, 2 days after, 3 days after, 4 days after, 5 days after, 10 days after, two weeks after, one month after, 1-3 months after, 3-6 months after, or 6-12 months after, or longer after administration of an anti-tumor drug. In specific embodiments, samples are taken 3 days after administration of an anti-tumor drug.

Markers

Methods provided herein use levels of various biomarkers to achieve the stated goal. In particular, useful markers herein are typically sequestered within either tumor cells (tumor specific biomarker) or within normal cells (control marker). Release of either tumor specific biomarkers or control markers to the circulation of a patient is indicative that the respective cell type, tumor or normal, has been damaged or killed. As such, the presence of control markers (particularly when elevated above a baseline level) in the circulation of a patient is an indicator of cell damage and a comparison of levels released by tumor cells to normal cells provides an index or indication of whether and at what level cancer and normal cells are being killed or damaged in response to the anti-tumor drug. Non-invasive detection and measurement of these markers before and after treatment with a proposed anti-tumor drug can be used to identify, adjust the dose, and determine the efficacy of any one anti-tumor drug on any one patient and for any one type of tumor. In some embodiments, the markers are tumor-responsive biomarkers that change in response to tumor burden but are not necessarily derived from the tumor.

Biomarkers herein can be a nucleic acid, peptide, protein, lipid, antigen, carbohydrate or proteoglycan, such as DNA (including, for example, cell-free DNA (cfDNA)) or RNA. The RNA can be mRNA, miRNA, snoRNA, snRNA, rRNAs, tRNAs, siRNA, hnRNA, or shRNA. The cfDNA alterations can include point mutations, DNA hypermethylations, microsatellite instabilities, and losses of heterozygosity. Detecting a plurality of biomarkers can, in some embodiments, provide greater sensitivity or specificity as compared to detecting less than a plurality of biomarkers.

Exemplary tumor cell-specific miRNAs include, but are not limited to, miR-9, miR-15b, miR-15a/miR-16-1, miR-17-3, miR-20a, miR-21, miR-24, miR-25, miR-26a, miR-27, miR-28, miR-30c, miR-92, miR-96-5p, miR-107, miR-122, miR-125a, miR-125a-3p, miR-126, miR-141, miR-145, miR-145-5p, miR-148b, miR-155, miR-182, miR-183-5p, miR-192, miR-194, miR-195, miR-199a, miR-200 family, miR-200a, miR-200b, miR-210, miR-221, miR-221-5p, miR-222, miR-223, miR-298, miR-324-5p, miR-346, miR-375, miR-378, miR-409-3p, miR-423-5p, miR-491, miR-574-3p, miR-622, miR-629, miR-671-3p, miR-1285, let-7c, and let-7e. Exemplary tumor-responsive miRNA biomarkers also include, but are not limited to, miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-885-5p, miR-376a, miR-1265, miR-623, miR-15a, miR-629, miR-30d-3p, miR-483-5p, miR-708-3p.

In some embodiments, an increase in the level of tumor-responsive miRNA biomarker in a sample obtained from a patient having cancer following administration of an anti-tumor drug is indicative of efficacy of the anti-tumor drug. Exemplary tumor-responsive miRNA biomarkers that increase following administration of an effective anti-tumor drug include, but are not limited to, miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-647, miR-885-5p, miR-376a, miR-1265, miR-623, miR-15a, miR-629, miR-30d-3p, miR-483-5p, miR-708-3p, and a combination thereof.

In certain embodiments, an increase in the level of lung tumor biomarker miRNA in a sample obtained from a patient having lung cancer following administration of an anti-tumor drug is indicative of efficacy of the anti-tumor drug against lung tumors. Exemplary lung tumor-responsivemiRNA biomarkers that increase following administration of an effective anti-tumor drug include, but are not limited to miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, and a combination thereof.

In certain embodiments, an increase in the level of prostate tumor miRNA biomarkers in a sample obtained from a patient having prostate cancer following administration of an anti-tumor drug is indicative of efficacy of the anti-tumor drug against prostate tumors. Exemplary prostate tumor-responsive miRNA biomarkers that increase following administration of an effective anti-tumor drug include, but are not limited to miR-181-a2, miR-1468, miR-634, miR-647, miR-885-5p, miR-376a, miR-1265, miR-623, miR-15a, miR-629, and a combination thereof.

In certain embodiments, an increase in the level of colon tumor miRNA biomarkers in a sample obtained from a patient having colon cancer following administration of an anti-tumor drug is indicative of efficacy of the anti-tumor drug against colon tumors. Exemplary colon tumor-responsive miRNA biomarkers that increase following administration of an effective anti-tumor drug include, but are not limited miR-30d-3p, miR-483-5p, miR-708-3p, and a combination thereof.

In some embodiments, a decrease in the level of tumor-responsive miRNA biomarkers in a sample obtained from a patient having cancer following administration of an anti-tumor drug is indicative of efficacy of the anti-tumor drug. Exemplary tumor-responsive miRNA biomarkers that decrease following administration of an effective anti-tumor drug include, but are not limited to, miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, and a combination thereof.

In certain embodiments, a decrease in the level of lung tumor miRNA biomarkers in a sample obtained from a patient having lung cancer following administration of an anti-tumor drug is indicative of efficacy of the anti-tumor drug against lung tumors. Exemplary lung tumor-responsive miRNA biomarkers that decrease following administration of an effective anti-tumor drug include, but are not limited to miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, and a combination thereof.

In certain embodiments, a decrease in the level of prostate tumor miRNA biomarkers in a sample obtained from a patient having prostate cancer following administration of an anti-tumor drug is indicative of efficacy of the anti-tumor drug against prostate tumors. Exemplary prostate tumor-responsive miRNA biomarkers that decrease following administration of an effective anti-tumor drug include, but are not limited to miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, and a combination thereof.

In certain embodiments, a decrease in the level of colon tumor miRNA biomarkers in a sample obtained from a patient having colon cancer following administration of an anti-tumor drug is indicative of efficacy of the anti-tumor drug against colon tumors. Exemplary colon tumor-responsive miRNA biomarkers that decrease following administration of an effective anti-tumor drug include, but are not limited to miR-21-3p, miR-101-5p, miR-122-3p, miR-197-3p, miR-429, miR-501-3p, miR-509-3p, miR-598, miR-206, miR-885-5p, miR-1972, and a combination thereof.

Exemplary cancer cell-specific proteins include, but are not limited to, BLK, transglutaminase 4 (TGM4), acid phosphatase (ACPP), CD20, prostate-specific membrane antigen (PSMA), B lymphoid tyrosine kinase (BLK), carcinoembryonic antigen, cytokeratin 19 fragment, cancer antigen 125, cancer antigen 15-3, cancer antigen 19-9, BRCA-1, BRCA-2, hCG, thyroglobulin, Hsp27, Hsp70, TGFβ, and alphafetoprotein.

Exemplary cancer cell-specific cell free DNA molecules include DNA with mutations in EGFR, TP53, KRAS, CD98, cathepsin D, and BRAF, epigenetic changes to glutathione S-transferase P1 and septin 9 genes, and hypermethylation of CDKN2a and APC genes.

Other miRNAs, cell free DNAs, and proteins are known to those skilled in the art and contemplated herein.

In some embodiments, a nucleic acid sequence (e.g., DNA, RNA, mRNA, miRNA, cell free DNA) can be used as a biomarker, but any relevant polypeptide sequence encoded thereby can also be used as a biomarker. Accordingly, reference to detection or measurement of a biomarker can refer to detection or measurement of either or both of a polynucleotide or polypeptide sequence. Biomarkers also include indicators of epigenetic changes, such as, for example, DNA methylation, mRNA methylation, histone modification, microRNAs, siRNAs, different splice forms of RNA, or double stranded RNA.

Exemplary non-specific or control markers include, for example, lactate dehydrogenase (LDH), glutathione reductase (GR), and fatty acid binding proteins (FABP, including L-FABP and I-FABP), kidney injury molecule-1 (Kim-1), S-100B, and neurone specific enolase (NSE). MicroRNA which indicates acute tissue injury includes miR-208, miR-133, miR-192, miR-1, miR-122, and miR-124. Other non-specific or control markers known to those skilled in the art are contemplated herein.

Monitoring, measuring, detecting, determining, or observing can be at the protein or nucleic acid level. Thus, the biomarkers include these proteins and the genes encoding these proteins. Where detection is at the protein level, the biomarker protein comprises the full-length polypeptide or any detectable fragment thereof, and can include variants of these protein sequences. Similarly, where detection is at the nucleotide level, the biomarker nucleic acid includes DNA comprising the full-length coding sequence, a fragment of the full-length coding sequence, variants of these sequences, for example naturally occurring variants or splice-variants, or the complement of such a sequence. Biomarker nucleic acids also include RNA, for example, mRNA, comprising the full-length sequence encoding the biomarker protein of interest, a fragment of the full-length RNA sequence of interest, or variants of these sequences. Biomarker proteins and biomarker nucleic acids also include variants of these sequences. By "fragment" is intended a portion of the polynucleotide or a portion of the amino acid sequence and hence protein encoded thereby. Polynucleotides that are fragments of a biomarker nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs known in the art. The protein and corresponding coding sequence for each of these markers is known in the art.

Biomarkers can be classified based on function. For example, biomarkers can be involved in DNA replication, cell survival/death, ribosome biogenesis, regulation of signal transduction, and regulation of progression through the cell cycle, MAP kinase phosphatase activity, transcription factor activity, cell proliferation, cell-cell signaling, and regulation from a PolII promoter. Accordingly, it is contemplated, that additional genes and encoded proteins that fall within these functional classifications could be useful biomarkers according to the methods described herein.

Methods provided herein measure the release of microRNAs (and other cytosolic or nuclear macromolecules normally contained within cells) from specific classes of tumor cells compared to release of similar markers specific for normal cells, to determine extent and ratio of tumor kill to normal cell kill. Methods are also provided herein that measure the retention of microRNAs from specific classes of tumor cells compared to the retention of similar markers specific for normal cells, to determine the extent and ratio of tumor kill to normal cell kill. Further provided are methods that measure the general response of a marker to an anti-tumor drug wherein the marker is not necessarily from a tumor.

In some aspects, the tumor is prostate cancer, and the tumor cell-specific marker is a microRNA selected from the group consisting of miR-96-5p, miR-183-5p, miR-145-5p, and miR-221-5p. Tumor-responsive miRNA biomarkers specific for prostate cancer can also include, miR-181-a2, miR-1468, miR-634, miR-647, miR-885-5p, miR-376a, miR-1265, miR-623, miR-15a, miR-629, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, and a combination thereof. In some aspects, the tumor cell-specific marker is prostate-specific membrane antigen (PSMA).

In certain aspects, the tumor is lung cancer and the tumor-responsive biomarker is a microRNA including miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, and a combination thereof.

In certain aspects, the tumor is colon cancer and the tumor-responsive biomarker is a microRNA including miR-30d-3p, miR-483-5p, miR-708-3p, miR-21-3p, miR-101-5p, miR-122-3p, miR-197-3p, miR-429, miR-501-3p, miR-509-3p, miR-598, miR-206, miR-885-5p, miR-1972, and a combination thereof.

In some aspects, the biomarker in the sample is measured and compared to the level of a control or general marker of cell toxicity such as, e.g., lactate dehydrogenase or glutathione reductase.

Some biomarkers useful herein represent known genes, the sequences of which are available through public databases known to those of skill in the art.

In some embodiments, the methods described herein use biomolecules (such as RNA, microRNA, protein, or DNA) that are normally sequestered within a cancer cell (e.g., cytosolic, nuclear, organellar, membrane-bound, etc.) and are specific to a tumor cell, but are released from the tumor cell when it is damaged or killed by the therapeutic agent. Such biomolecules would include, but are not limited to: RNA or DNA or protein that contain mutations that are specific to the cancer cells; single or multiple species of microRNA that are characteristic of the tumor cell; or RNA, DNA, or proteins that are specific to the cell lineage from which the cancer originated. An increase in such a biomarker is an indication of tumor cell killing, and can, in some aspects, be compared to the level of a general marker of cell toxicity (i.e., not specific to the tumor cell), such as lactate dehydrogenase (LDH) or glutathione reductase (GR). In some aspects, the level of such a biomarker following administration of an anti-tumor drug can be compared to the level of the biomarker prior to administration of the anti-tumor drug in order to determine efficacy of the anti-tumor drug.

In certain embodiments, the methods described herein use biomolecules (such as miRNA) that are normally released by a cancer cell and are specific to tumor cells, or a specific type of tumor cell, but are sequestered within a cancer cell when it is damaged or killed by the therapeutic agent. Such biomolecules include single or multiple species of microRNA that are characteristic of tumor cells or specific types of tumor cells (e.g., lung cancer or prostate cancer). A decrease in such a biomarker is an indication of tumor cell killing or damage and can, in some aspects, be compared to the level of a general marker of cell toxicity (i.e., not specific to the tumor cell), such as lactate dehydrogenase (LDH) or glutathione reductase (GR). In some aspects, the level of such a biomarker following administration of an anti-tumor drug can be compared to the level of the biomarker prior to administration of the anti-tumor drug in order to determine efficacy of the anti-tumor drug. In specific embodiments, the tumor-responsive biomarkers are not released by the tumor cell, but are released by the tumor host in response to the presence of the tumor. Thus, the tumor-responsive biomarkers may be either directly or inversely proportional to the tumor burden.

Detection and Quantitation of Biomarkers

Any suitable method can be used to detect (a differential presence of) one or more of the biomarkers described herein. Successful practice of the invention can be achieved with one or a combination of methods that can detect and/or quantify the biomarkers. These methods include, without limitation, hybridization-based methods including those employed in biochip arrays, mass spectrometry (e.g., laser desorption/ionization mass spectrometry), fluorescence (e.g., sandwich immunoassay), surface plasmon resonance, ellipsometry and atomic force microscopy. For nucleic acid biomarkers, methods for detection and quantitation include PCR, quantitative PCR, northern blot analysis, southern blot analysis, mass spectrometry and the like.

Other methods are well known in the art and include but are not limited to western blots, ELISA, immunoprecipitation, immunofluorescence, flow cytometry, and immunohistochemistry. In particular embodiments, expression of a biomarker is detected on a protein level using, for example, antibodies that are directed against specific biomarker proteins. These antibodies can be used in various methods such as Western blot, ELISA, multiplexing technologies, immunoprecipitation, or immunohistochemistry techniques. In some embodiments, detection of certain markers is accomplished by electrochemiluminescence (ECL).

Methods may further include, by one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$_n$, atmospheric pressure photoionization mass spectrometry (APPI-MS), APPI-MS/MS, and APPI-(MS)$_n$, quadrupole mass spectrometry, Fourier transform mass spectrometry (FTMS), and ion trap mass spectrometry, where n is an integer greater than zero.

In one embodiment, microarray analysis is used to detect microRNA, known as microRNA or miRNA expression profiling. The microarray for detection of microRNA may be a microarray platform, wherein the probes of the microarray may be comprised of antisense miRNAs or DNA oligonucleotides. In the first case, the target is a labelled sense miRNA sequence, and in the latter case the miRNA has been reverse transcribed into cDNA and labelled.

The microarray for detection of microRNA may be a commercially available array platform, such as NCode™ miRNA Microarray Expression Profiling (Invitrogen), miRCURY LNA™ microRNA Arrays (Exiqon), microRNA Array (Agilent), .mu.Paraflo® Microfluidic Biochip Technology (LC Sciences), MicroRNA Profiling Panels (Illumina), Geniom® Biochips (Febit Inc.), microRNA Array (Oxford Gene Technology), Custom AdmiRNA™ profiling service (Applied Biological Materials Inc.), microRNA Array (Dharmacon—Thermo Scientific), LDA TaqMan analyses (Applied Biosystems), Taqman microRNA Array (Applied Biosystems) or any other commercially available array.

Microarray analysis may comprise all or a subset of the steps of RNA isolation, RNA amplification, reverse transcription, target labelling, hybridization onto a microarray chip, image analysis and normalization, and subsequent data analysis; each of these steps may be performed according to a manufacturers protocol.

It follows, that any of the methods as disclosed herein above e.g. for diagnosing of an individual may further comprise one or more of the steps of:
  i) isolating miRNA from a sample,
  ii) labelling of said miRNA,
  iii) hybridizing said labelled miRNA to a microarray comprising miRNA-specific probes to provide a hybridization profile for the sample,
  iv) performing data analysis to obtain a measure of the miRNA expression profile of said sample.

In another embodiment, the microarray for detection of microRNA is custom made.

A probe or hybridization probe is a fragment of DNA or RNA of variable length, which is used to detect in DNA or RNA samples the presence of nucleotide sequences (the target) that are complementary to the sequence in the probe. One example is a sense miRNA sequence in a sample (target) and an antisense miRNA probe. The probe thereby hybridizes to single-stranded nucleic acid (DNA or RNA) whose base sequence allows probe-target base pairing due to complementarity between the probe and target.

To detect hybridization of the probe to its target sequence, the probe or the sample is tagged (or labeled) with a molecular marker. Detection of sequences with moderate or high similarity depends on how stringent the hybridization conditions were applied—high stringency, such as high hybridization temperature and low salt in hybridization buffers, permits only hybridization between nucleic acid sequences that are highly similar, whereas low stringency, such as lower temperature and high salt, allows hybridization when the sequences are less similar. Hybridization probes used in microarrays refer to nucleotide sequences covalently attached to an inert surface, such as coated glass slides, and to which a mobile target is hybridized. Depending on the method the probe may be synthesized via phosphoramidite technology or generated by PCR amplification or cloning (older methods). To design probe sequences, a probe design algorithm may be used to ensure maximum specificity (discerning closely related targets), sensitivity (maximum hybridization intensities) and normalized melting temperatures for uniform hybridization.

Systems

In another embodiment of the invention, the output from a detection device can subsequently be processed, stored, and further analyzed or assayed using a bio-informatics system. A bio-informatics system may include one or more of the following, without limitation: a computer; a plurality of computers connected to a network; a signal processing tool(s); a pattern recognition tool(s); a tool(s) to control flow rate for sample preparation, separation, and detection.

The data processing utilizes mathematical foundations. In another embodiment of the invention, dynamic programming is used to align a separation axis with a standard separation profile. Intensities may be normalized, for example, by fitting roughly 90% of the intensity values into a standard spectrum. The data sets can then be fitted using wavelets designed for separation and mass spectrometer data. In yet another embodiment of the invention, data processing filters out some of the noise and reduces spectrum dimensionality, potentially allowing for pattern recognition.

Following data processing, pattern recognition tools can be utilized to identify subtle differences between phenotypic states. Pattern recognition tools are based on a combination of statistical and computer scientific approaches, which provide dimensionality reduction. Such tools are scalable. Data so obtained may be stored on a computer readable medium.

Kits

In one aspect, the invention provides kits for qualifying cancer status in a subject, wherein the kits can be used to detect the differential presence of the biomarkers described herein. For example, the kits can be used to detect a differential presence of any combination of the biomarkers in tumor samples of subjects before and after exposure to a therapeutic drug. The kits of the invention have many applications. For example, the kits can be used to monitor efficacy of a therapeutic drug in a cancer subject. The kits can also be used to identify agents useful in the treatment of cancer.

In specific embodiments, kits of the invention contain an assay for a biomarker, which is optionally isotopically or fluorescently labeled.

The kits of the invention may include instructions, reagents, testing equipment (test tubes, reaction vessels, needles, syringes, etc.), standards for calibration, and/or equipment. Reagents may include acids, bases, oxidizing agents, and marker species. The instructions provided in a kit according to the invention may be directed to suitable operational parameters in the form of a label or a separate insert.

The kits may also include an adsorbent, wherein the adsorbent retains one or more biomarkers described herein (polynucleotide or polypeptide), and written instructions for use of the kit for qualification of cancer status in a subject. Such a kit could, for example, comprise: (a) a substrate comprising an adsorbent thereon, wherein the adsorbent is suitable for binding a biomarker, and (b) instructions to detect the biomarker(s) by contacting a sample with the adsorbent and detecting the product(s) retained by the adsorbent. Accordingly, the kit could comprise (a) a DNA probe that specifically binds to a biomarker; and (b) a detection reagent. Such a kit could further comprise an eluent (as an alternative or in combination with instructions) or instructions for making an eluent, wherein the combination of the adsorbent and the eluent allows detection of the biomarker using, for example, gas phase ion spectrometry.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

Articles of Manufacture

The methods and materials described herein can be used to, e.g., determine efficacy of a putative anti-cancer drug and to aid a medical practitioner in selecting an appropriate therapy for the subject. To aid in this selection, it may be useful for medicaments used for treating a given cancer (such as any of the therapies comprising an anti-cancer agent described herein) to contain information or appropriate labels indicating that the medicaments should be prescribed (and/or administered) to a subject having an having an increase in the level of a given tumor cell-specific marker following a first administration (or test administration) of a putative anti-tumor drug. Thus, the disclosure also features an article of manufacture comprising: a container; and a composition contained within the container, wherein the composition comprises an active agent for treating a given cancer in a subject and wherein the container has a label indicating that the composition is for use in treating that cancer in a subject if a sample obtained from the subject after the first administration contains an amount of a tumor cell-specific marker greater than the control amount of that same marker. The article of manufacture can also contain instructions for administering the active agent to the subject.

Numbered Embodiments

1. A method of controlling dosage of an anti-tumor drug administered to a patient having cancer, comprising:
determining a first level of at least one tumor-responsive biomarker in a first biological sample of the patient, wherein the first sample is obtained before administering to the patient a first dose of an anti-tumor drug;
determining a second level of the at least one tumor-responsive biomarker in a subsequent biological sample of the patient, wherein the subsequent sample is obtained after administering to the patient the first dose of the anti-tumor drug;
wherein thereafter, the patient receives a second dose of the anti-tumor drug, wherein the dosage regimen of the second dose depends on whether a decrease or increase in the level of the tumor-responsive biomarker is identified in the subsequent biological sample of the patient following administration of the first dose of the anti-tumor drug.

2. The method of embodiment 1, wherein the at least one tumor-responsive biomarker includes an miRNA marker selected from the group consisting of: miR-802, miR-30b-3p, miR-510, miR-622, miR-127-3p, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-885-5p, miR-376a, miR-1265, miR-623, miR-15a, miR-629, miR-30d-3p, miR-483-5p, miR-708-3p, and a combination thereof.

3. The method of any one of embodiments 1 or 2, wherein the dosage regimen of the anti-tumor drug is changed if the level of the at least one tumor-responsive biomarker is not increased.

4. The method of any one of embodiments 1-3, wherein the at least one tumor-responsive biomarker includes at least one miRNA marker selected from the group consisting of: miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-647, miR-885-5p, miR-376a, miR-1265, miR-623, miR-15a, miR-629, miR-30d-3p, miR-483-5p, miR-708-3p, and a combination thereof.

5. The method of any one of embodiments 1-4, wherein the cancer is lung cancer and the at least one tumor-responsive biomarker includes at least one miRNA marker selected from the group consisting of: miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, and a combination thereof.

6. The method of any one of embodiments 1-4, wherein the cancer is prostate cancer and the at least one tumor-responsive biomarker includes at least one miRNA marker selected from the group consisting of: miR-181-a2, miR-1468, miR-634, miR-647, miR-885-5p, miR-376a, miR-1265, miR-623, miR-15a, miR-629, and a combination thereof.

7. The method of any one of embodiments 1-4, wherein the cancer is colon cancer and the at least one tumor-responsive biomarker includes at least one miRNA marker selected from the group consisting of: miR-30d-3p, miR-483-5p, miR-708-3p, and a combination thereof.

8. The method of any one of embodiments 1 or 2, wherein the dosage regimen of the anti-tumor drug is changed if the level of the at least one tumor-responsive biomarker is not decreased.

9. The method of embodiment 1, 2, or 8, wherein the at least one tumor-responsive biomarker includes at least one miRNA marker selected from the group consisting of: miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, and a combination thereof.

10. The method of embodiment 1, 2, 8, or 9, wherein the cancer is lung cancer, and the at least one tumor-responsive biomarker includes at least one miRNA marker selected from the group consisting of: miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, and a combination thereof.

11. The method of embodiment 1, 2, 8, or 9, wherein the cancer is prostate cancer, and the at least one tumor-responsive biomarker includes at least one miRNA marker selected from the group consisting of: miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, and a combination thereof.

12. The method of embodiment 1, 2, 8, or 9, wherein the cancer is colon cancer, and the at least one tumor-responsive biomarker includes at least one miRNA marker selected from the group consisting of: miR-21-3p, miR-101-5p, miR-122-3p, miR-197-3p, miR-429, miR-501-3p, miR-509-3p, miR-598, miR-206, miR-885-5p, miR-1972, and a combination thereof.

13. The method of any one of embodiments 1-12, further comprising:
determining the amount of a control marker before and after administering to the patients the first dose of the anti-tumor drug, wherein the second dose of the anti-tumor drug is adjusted according to the change in the level of the tumor-responsive biomarker compared to the change in the level of the control marker in the determining step,
wherein the control marker is different from the tumor-responsive biomarker.

14. The method of any one of embodiments 1-13, wherein the tumor is selected from the group consisting of non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lymphoblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, Waldenstrom's Macroglobulinemia, mantle cell lymphoma, heavy chain disease, lung carcinoma, breast carcinoma, ovarian carcinoma, skin carcinoma, colon carcinoma, urinary bladder carcinoma, liver carcinoma, gastric carcinoma, prostate cancer, renal cell carcinoma, nasopharyngeal carcinoma, squamous cell carcinoma, thyroid papillary carcinoma, cervical carcinoma, and sarcomas.

15. The method of any one of embodiments 1-14, wherein the first biological sample and the second biological sample are fluid samples obtained from blood, plasma, serum, cerebrospinal fluid, synovial fluid, lymph, saliva, or urine of the patient.

16. The method of any one of embodiments 1-15, wherein the second biological sample is obtained from the patient immediately after, 6 hours after, 12 hours after, 1 day after, 2 days after, 3 days after, 4 days after, 5 days after, 10 days after, two weeks after, one month after, 1-3 months after, 3-6 months after, or 6-12 months after administration of the first dose of the anti-tumor drug.

17. The method of any one of embodiments 1-16, wherein the therapeutic efficacy of the anti-tumor drug increases following administration of the second dose of the anti-tumor drug.

18. The method of any one of embodiments 1-17, wherein the anti-tumor drug includes cisplatin, docetaxel, or irinotecan.

19. The method of any one of embodiments 1-18, wherein the second dose of the anti-tumor drug is administered along with a different anti-tumor drug.

20. A method for administering at least one anti-tumor drug in two separate doses to a patient having cancer, comprising:
(a) obtaining a first biological sample from the patient;
(b) determining a baseline level of at least one tumor-responsive biomarker in the first biological sample;
(c) administering the first dose of an anti-tumor drug to the patient;
(d) obtaining a second biological sample from the patient;
(e) determining a first level of the at least one tumor-responsive biomarker in the second biological sample;
(f) comparing the baseline level and the first level of tumor-responsive biomarker to identify if the patient has a decrease or increase in the level of the at least one tumor-responsive biomarker; and
(g) administering the second dose of the anti-tumor drug to the patient,
wherein the dosage regimen of the second dose is changed if the patient has a decrease or increase in the level of the at least one tumor-responsive biomarker.

21. The method of embodiment 20, wherein the at least one tumor-responsive biomarker includes at least one miRNA marker selected from the group consisting of: miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-885-5p, miR-376a, miR-1265, miR-623, miR-15a, miR-629, miR-30d-3p, miR-483-5p, miR-708-3p, and a combination thereof.

22. The method of embodiment 20 or 21, wherein the dosage regimen of the anti-tumor drug is changed if the level of the at least one tumor-responsive biomarker is not increased.

23. The method of any one of embodiments 20-22, wherein the at least one tumor-responsive biomarker includes at least one miRNA marker selected from the group consisting of: miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-647, miR-885-5p, miR-376a, miR-1265, miR-623, miR-15a, miR-629, miR-30d-3p, miR-483-5p, miR-708-3p, and a combination thereof.

24. The method of any one of embodiments 20-23, wherein the cancer is lung cancer and the at least one tumor-responsive biomarker includes at least one miRNA marker selected from the group consisting of: miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, and a combination thereof.

25. The method of any one of embodiments 20-23, wherein the cancer is prostate cancer and the at least one tumor-responsive biomarker includes at least one miRNA marker selected from the group consisting of: miR-181-a2, miR-1468, miR-634, miR-647, miR-885-5p, miR-376a, miR-1265, miR-623, miR-15a, miR-629, and a combination thereof.

26. The method of any one of embodiments 20-23, wherein the cancer is colon cancer and the at least one tumor-responsive biomarker includes at least one miRNA marker selected from the group consisting of: miR-30d-3p, miR-483-5p, miR-708-3p, and a combination thereof.

27. The method of embodiment 20 or 21, wherein the dosage regimen of the anti-tumor drug is changed if the level of the at least one tumor-responsive biomarker is not decreased.

28. The method of embodiment 20, 21, or 27, wherein the at least one tumor-responsive biomarker includes at least one miRNA marker selected from the group consisting of: miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, and a combination thereof.

29. The method of embodiment 20, 21, 27, or 28, wherein the cancer is lung cancer, and the at least one tumor-responsive biomarker includes at least one miRNA marker selected from the group consisting of: miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, and a combination thereof.

30. The method of embodiment 20, 21, 27, or 28, wherein the cancer is prostate cancer, and the at least one tumor-responsive biomarker includes at least miRNA marker selected from the group consisting of: miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, and a combination thereof.

31. The method of embodiment 20, 21, 27, or 28, wherein the cancer is colon cancer, and the at least one tumor-responsive biomarker includes at least one miRNA marker selected from the group consisting of: miR-21-3p, miR-101-5p, miR-122-3p, miR-197-3p, miR-429, miR-501-3p, miR-509-3p, miR-598, miR-206, miR-885-5p, miR-1972, and a combination thereof.

32. The method of any one of embodiments 20-31, wherein the tumor is selected from the group consisting of non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lymphoblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, Waldenstrom's Macroglobulinemia, mantle cell lymphoma, heavy chain disease, lung carcinoma, breast carcinoma, ovarian carcinoma, skin carcinoma, colon carcinoma, urinary bladder carcinoma, liver carcinoma, gastric carcinoma, prostate cancer, renal cell carcinoma, nasopharyngeal carcinoma, squamous cell carcinoma, thyroid papillary carcinoma, cervical carcinoma, and sarcomas.

33. The method of any one of embodiments 20-32, wherein the first biological sample and the second biological sample are fluid samples obtained from blood, plasma, serum, cerebrospinal fluid, synovial fluid, lymph, saliva, or urine of the patient.

34. The method of any one of embodiments 20-33, wherein the second biological sample is obtained from the patient immediately after, 6 hours after, 12 hours after, 1 day after, 2 days after, 3 days after, 4 days after, 5 days after, 10 days after, two weeks after, one month after, 1-3 months after, 3-6 months after, or 6-12 months after administration of the first dose of the anti-tumor drug.

35. The method of any one of embodiments 20-34, wherein the therapeutic efficacy of the anti-tumor drug increases following administration of the second dose of the anti-tumor drug.

36. The method of any one of embodiments 20-35, wherein the anti-tumor drug includes cisplatin, docetaxel, or irinotecan.

37. The method of any one of embodiments 20-36, wherein the second dose of the anti-tumor drug is administered along with a different anti-tumor drug.

38. A method of selecting at least one anti-tumor drug, the method comprising:
determining the level of at least one tumor-responsive biomarker before and after administering a candidate anti-tumor drug to a host non-human animal having a tumor; and selecting an anti-tumor drug if the candidate anti-tumor drug increases or decreases the level of the at least one tumor-responsive biomarker in the host non-human animal.

39. The method of embodiment 38, wherein the at least one selected anti-tumor drug is formulated into a composition.

40. The method of embodiment 38, further comprising:
(a) providing a host non-human animal having a tumor;
(b) obtaining a first biological sample from the host non-human animal;
(c) determining the baseline level of at least one tumor-responsive biomarker in the first biological sample;
(d) administering a candidate anti-tumor drug to the host non-human animal;
(e) obtaining a second biological sample from the host non-human animal;
(f) determining a first level of the at least one tumor-responsive biomarker in the second biological sample;
(g) comparing the baseline level and the first level of the tumor-specific miRNA marker to identify if the patient has a decrease or increase in the level of the at least one tumor-responsive biomarker; and
(h) selecting the candidate anti-tumor drug as an anti-tumor drug if administration of the candidate anti-tumor drug leads to the increase or decrease in the level of the tumor-responsive biomarker in the host non-human animal.

41. The method of any one of embodiments 38-40, wherein the at least one tumor-responsive biomarker includes at least one miRNA marker selected from the group consisting of: miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-885-5p, miR-376a, miR-1265, miR-623, miR-15a, miR-629, miR-30d-3p, miR-483-5p, miR-708-3p, and a combination thereof.

42. The method of any one of embodiments 38-41, wherein the candidate anti-tumor drug is selected if the level of the at least one tumor-responsive biomarker is increased.

43. The method of any one of embodiments 38-42, wherein the at least one tumor-responsive biomarker includes at least one miRNA marker selected from the group consisting of: miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, miR-181-a2, miR-1468, miR-634, miR-647, miR-885-5p, miR-376a, miR-1265, miR-623, miR-15a, miR-629, miR-30d-3p, miR-483-5p, miR-708-3p, and a combination thereof.

44. The method of any one of embodiments 38-42, wherein the cancer is lung cancer and the at least one tumor-responsive biomarker includes at least one miRNA marker selected from the group consisting of: miR-335-3p, miR-16-5p, miR-361-5p, miR-27a-5p, miR-24-3p, miR-1260a, miR-192-5p, miR-548h-5p, miR-122-5p, miR-1208, miR-215, miR-30a-3p, miR-588, miR-10a-3p, miR-21-5p, miR-382-3p, miR-15b-3p, miR-19b-3p, miR-543, miR-1271-5p, miR-106a-5p, miR-106b-5p, miR-520h, and a combination thereof.

45. The method of any one of embodiments 38-42, wherein the cancer is prostate cancer and the at least one tumor-responsive biomarker includes at least one miRNA marker selected from the group consisting of: miR-181-a2, miR-1468, miR-634, miR-647, miR-885-5p, miR-376a, miR-1265, miR-623, miR-15a, miR-629, and a combination thereof.

46. The method of any one of embodiments 38-42, wherein the cancer is colon cancer and the at least one tumor-responsive biomarker includes at least one miRNA marker selected from the group consisting of: miR-30d-3p, miR-483-5p, miR-708-3p, and a combination thereof.

47. The method of any one of embodiments 38-41, wherein the candidate anti-tumor drug is selected if the level of the at least one tumor-responsive biomarker is decreased.

48. The method of any one of embodiments 38-41 or 47, wherein the at least one tumor-responsive biomarker includes at least one miRNA marker selected from the group consisting of: miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, miR-21-3p, miR-101-5p, miR-122-3p, miR-197-3p, miR-429, miR-501-3p, miR-509-3p, miR-598, miR-206, miR-885-5p, miR-1972, and a combination thereof.

49. The method of any one of embodiments 38-41, 47, or 48, wherein the cancer is lung cancer, and the at least one tumor-responsive biomarker includes at least one miRNA marker selected from the group consisting of: miR-802, miR-30b-3p, miR-510, miR-622, miR-127-3p, miR-373-5p, miR-298, miR-302b-3p, miR-367-3p, miR-181b-5p, miR-518a-3p, miR-155-5p, miR-214-3p, miR-329, let-7f-5p, miR-190b, miR-503-5p, miR-92a-1-5p, miR-647, miR-153, miR-93-5p, miR-20a-5p, miR-221-3p, miR-378a-3p, miR-221-3p, miR-20a5p, miR-93-5p, and a combination thereof.

50. The method of any one of embodiments 38-41, 47, or 48, wherein the cancer is prostate cancer, and the at least one tumor-responsive biomarker includes at least one miRNA marker selected from the group consisting of: miR-190, miR-153, miR-26a-2, miR-518c, miR-503, miR-337-3p, miR-518f, miR-370, miR-92a-1, miR-526b, miR-1238, miR-886-3p, miR-887, miR-23a, miR-1267, miR-621, miR-515-3p, miR-424, miR-20b, miR-202, and a combination thereof.

51. The method of any one of embodiments 38-41, 47, or 48, wherein the cancer is colon cancer, and the at least one tumor-responsive biomarker includes at least one miRNA marker selected from the group consisting of: miR-21-3p, miR-101-5p, miR-122-3p, miR-197-3p, miR-429, miR-501-3p, miR-509-3p, miR-598, miR-206, miR-885-5p, miR-1972, and a combination thereof.

52. The method of any one of embodiments 38-51, further comprising introducing a tumor cell, a tumor tissue, or a tumor organ into the host non-human animal to provide the host non-human animal having the tumor.

53. The method of any one of embodiments 38-52, wherein the tumor is derived from a human patient having a cancer, and wherein the non-human animal is a rodent.

EXAMPLES

The following examples are provided for illustrative purposes only and are not intended to limit the scope of the invention.

Example 1

The tumor cell being targeted is a B-cell lymphoma that expresses the cell surface protein CD20 (also called MS4A1). Drugs that target CD20-expressing cells, such as conventional antibodies, enhanced antibodies, or bispecific antibodies that engage other effector cells such as T-cells, cause damage to the B-cell lymphoma tumor cells and thereby release specific biomolecules that can be detected in the circulation.

In this example, mice bearing Raji cell tumors (a B-cell lymphoma tumor line) are treated with a bispecific antibody containing a CD20 binding arm and a CD3 binding arm (which engages effector T-cells and activates killing of the Raji cells). As a result of treatment of the mice with this CD20×CD3 bispecific reagent, increased levels of biomolecules that are specific to the Raji cells are found in the circulation of the mice. These biomolecules include cytosolic proteins such as B lymphoid tyrosine kinase (BLK) and DNA such as the specifically rearranged immunoglobulin gene from the Raji cell.

Example 2

The tumor cell being targeted is a prostate cancer cell that expresses prostate specific cell surface proteins such as FOLH1 (also called PSMA), Steap1, or Steap2. Drugs that target FOLH1-expressing cells, such as conventional antibodies, enhanced antibodies, or antibody drug conjugates that are linked to toxins, cause damage to the prostate tumor cells and thereby release specific biomolecules that can be detected in the circulation.

In this example, mice bearing LnCAP tumors (a prostate cancer tumor line) are treated with an antibody drug conjugate (ADC) consisting of an antibody directed to FOLH1 conjugated via a non-cleavable linker to a maytansinoid toxic drug. As a result of treatment of the mice with this FOLH1-directed ADC, increased levels of biomolecules that are specific to the LnCAP cells are found in the circulation of the mice. These biomolecules include cytosolic proteins such as transglutaminase 4 (TGM4) and acid phosphatase (ACPP), and DNA such as the TMPRSS2-ERG gene fusion that is common in prostate cancer. Further, treatment also changes the pattern of certain microRNA's that are found in the circulation; these microRNA's include miR's 96-5p, 183-5p, 145-5p, and 221-5p.

Example 3: Method of miRNA Profiling

Plasma samples (50 uL) were stored at −80° C. after receiving them. The samples were thawed on ice, and total RNA was isolated with the miRCURY RNA Isolation Kit for Biofluids (Exiqon) according to the supplied protocol (1 uL of Exiqon spike-in UniRT RNA mix was added to each sample before RNA isolation). RNA was eluted into 50 uL nuclease-free water, and either processed directly for cDNA synthesis of stored at −80° C. until that time. RNA from each sample was used to create cDNA in 40 uL reaction volume with the Universal cDNA Synthesis Kit II (Exiqon) according to the supplied protocol. RNA concentration for plasma samples is not quantitated; 8 uL each RNA sample is used without adjusting concentration. The 40 uL of cDNA per sample was then used to set-up qPCR directly or stored at −20° C. until use. The 40 uL cDNA was diluted into 4 mL of nuclease-free water, and then mixed with 4 mL 2× ExiLENT SYBR Green master mix (Exiqon) to create 8 mL qPCR mix, according to protocol supplied with miRNome Panels (Exiqon). The 8 ml master mix was then pipetted into the two 384-well plates (Exiqon microRNA Ready-to-Use PCR, Human panel I+II, V3.M), 10 ul per well according to the supplied protocol. The plates were briefly centrifuged, sealed, and run on the ABI Viia7 real time PCR thermocycler, using the PCR template program supplied by Exiqon. Results were exported as text files and then imported into the GenEx software (Exiqon) for analysis. Data pre-processing and analysis steps were performed according to the recommendations of the Exiqon Data Analysis Guide. Briefly, biological replicate were grouped, outliers were automatically detected and removed, Ct values higher than 37 were considered background and removed, missing data was filled by the GenEx software with an imputed value based on group mean. Cts for each sample were normalized to the global mean of all expressed miRNAs with a Ct<34. Various analyses could be done in GenEx, including clustering analysis and t-tests between different groups of samples to determine miRNAs significantly altered between groups.

Example 4: Drug Efficacy of COLO 205 Tumor Treated with Irinotecan

Immune compromised mice were injected with COLO 205 human colorectal cancer cells and tumors were allowed to develop, after which the mice were treated with either irinotecan or vehicle for 14 days. In a second control group, normal mice maintained in parallel but not bearing tumors were treated with either irinotecan or vehicle. A third control group consisted of tumor-bearing mice or normal, tumor-free mice that did not receive any treatment. During the course of drug treatment, blood plasma samples were taken from all mice at regular intervals from 3 to 14 days. RNA was prepared from the plasma samples and analyzed for miRNA content by a panel of quantitative PCR assays for approximately 700 miRNAs. The relative quantities of each miRNA assayed were normalized to the global mean in each sample and then compared between the paired groups: drug versus vehicle treatment in tumor-bearing mice; drug versus vehicle in tumor-free mice; and tumor bearing versus tumor-free mice. Samples were taken from six replicate mice for each time point in each of the categories. MicroRNAs whose mean values for the six replicates differed by a factor of at least two between the comparative categories and had a P value (Student's T-test) less than 0.05 were examined further.

After 14 days of drug treatment there was a significantly lower tumor burden in the drug treated mice than in the vehicle treated control group. Comparing the plasma miRNA profiles between the drug-treated and vehicle control group at the 14 day time point revealed many different, with some miRNAs more abundant and others less abundant in the drug treated mice compared with the controls. To eliminate those miRNA differences that were the result of drug treatment alone, we examined the miRNA profiles in the irinotecan treated normal, tumor-free mice compared with the same type of mice treated with vehicle. All miRNAs that showed the same directional differences (e.g. higher in the drug treated group than in the vehicle treated controls) that we observed in the tumor bearing experimental group were eliminated from consideration as part of a drug efficacy signature.

The miRNA profiles were examined in the plasma samples from the tumor-bearing mice treated with drug or vehicle for only three days, a time in the course of drug treatment where no significant difference in tumor burden was seen. We looked for miRNAs whose pattern of detection matched that in the mice treated with drug for 14 days. The result was the 14 miRNAs shown in Table 1. The pattern of quantification for these miRNAs—higher or lower in the drug treated mice compared to the vehicle treated controls—matched miRNAs from the 14 day time point. We found three miRNAs, miR-30d-3p, miR-483-5p, and miR-708-3p, that were elevated in the drug treated tumor bearing mice compared with the vehicle controls and 11 miRNAs, miR-21-3p, miR-101-5p, miR-122-3p, miR-197-3p, miR-429, miR-501-3p, miR-509-3p, miR-598, miR-206, miR-885-5p, and miR-1972, that were lower in the drug treated mice compared with the controls. These 14 miRNAs form a signature of plasma miRNA content that correlates with drug efficacy late in the course of drug treatment and predicts efficacy early in the drug treatment regimen before any effects of irinotecan on tumor burden could be detected.

To better understand and validate the drug efficacy signature, we looked at the content of the 14 signature miRNAs in untreated tumor bearing mice compared to normal tumor-free controls. The 11 miRNAs listed as having lower plasma contents in the drug treated mice compared with the controls (column 2 of Table 1) actually had the opposite pattern in the untreated tumor-bearing mice—they were detected in the tumor-bearing mice but were below the limit of detection in the normal controls. Detection of these miRNAs in plasma correlates with tumor load. Irinotecan treatment reversed this pattern—the 11 miRNAs went from detectable in the vehicle treated mice to undetectable in the drug treated mice, reflecting the efficacy of irinotecan at reducing tumor load. The three miRNAs listed as having higher plasma contents in the drug treated mice compared with the controls (left side of Table 1) showed a mirror pattern—they were detected in normal mice but were either reduced (miR-483-5p) or not detected at all (miR-30d-3p and miR-708-3p) in tumor-bearing mice, while irinotecan treatment in the tumor-bearing mice reversed this pattern; they either went from undetected to detected or, in the case of miR-483-5p, increased.

TABLE 1

Drug efficacy signature for COLO 205 tumor treated with irinotecan miRNAs different upon drug treatment*

| Higher | Lower |
|---|---|
| miR-30d-3p | miR-21-3p |
| | miR-101-5p |
| | miR-122-3p |
| | miR-197-3p |
| | miR-429 |
| miR-483-5p | |
| | miR-501-3p |
| | miR-509-3p |

TABLE 1-continued

Drug efficacy signature for COLO 205 tumor treated with irinotecan miRNAs different upon drug treatment*

| Higher | Lower |
|---|---|
| | miR-598 |
| | miR-206 |
| miR-708-3p | |
| | miR-885-5p |
| | miR-1972 |

*Relative to a vehicle-treated control

Thus, the 14 miRNAs in the COLO 205 drug efficacy signature serve as sensitive early predictors of irinotecan anti-tumor drug efficacy. At the same time they form a diagnostic signature of tumor load. The methods described herein to derive the drug efficacy signature for the COLO 205 tumor could be applied to other drug treatments and other human xenograft tumor models as well as genetically induced tumors. It would also be possible to apply the same methods to any disease situation for which effective therapies exist or are being developed.

While this invention has been described with an emphasis upon typical embodiments, it will be understood by those of ordinary skill in the art that variations of the typical embodiments may be used and that it is intended that the invention may be practiced otherwise than as specifically described herein. Accordingly, this invention includes all modifications encompassed within the spirit and scope of the invention as defined by the following claims.

What is claimed is:

1. A method of treating a colon cancer tumor in a human patient, said method comprising:
   (a) providing a host mouse having a xenograft of a colon cancer tumor of a patient;
   (b) obtaining a first plasma sample from the host mouse;
   (c) performing a first assay to detect a baseline level of each of miR-21-3p, miR-101-5p, miR-122-3p, miR-197-3p, miR-429, miR-501-3p, miR-509-3p, miR-598, miR-206, miR-885-5p, miR-1972, miR-30d-3p, miR-483-5p, and miR-708-3p in the first plasma sample;
   (d) administering a candidate anti-tumor drug to the host mouse;
   (e) obtaining a second plasma sample from the host mouse;
   (f) performing a second assay to detect a test level of each of miR-21-3p, miR-101-5p, miR-122-3p, miR-197-3p, miR-429, miR-501-3p, miR-509-3p, miR-598, miR-206, miR-885-5p, miR-1972, miR-30d-3p, miR-483-5p, and miR-708-3p in the second plasma sample, wherein the test level of each of miR-30d-3p, miR-483-5p, and miR-708-3p is higher than the baseline level, and the test level of each of miR-21-3p, miR-101-5p, miR-122-3p, miR-197-3p, miR-429, miR-501-3p, miR-509-3p, miR-598, miR-206, miR-885-5p, and miR-1972 is lower than the baseline level; and
   (g) administering the candidate anti-tumor drug to the human patient.

2. The method of claim 1, wherein the candidate anti-tumor drug is formulated into a composition.

3. The method of claim 1, further comprising introducing a tumor cell, a tumor tissue, or a tumor organ into the host mouse to provide the host mouse having the tumor.

* * * * *